United States Patent
Hoshen et al.

(10) Patent No.: US 9,988,690 B2
(45) Date of Patent: Jun. 5, 2018

(54) COMPOSITIONS AND METHODS FOR PROGNOSIS OF OVARIAN CANCER

(71) Applicants: ROSETTA GENOMICS LTD., Rehovot (IL); MOR RESEARCH APPLICATIONS, Tel Aviv (IL)

(72) Inventors: Moshe Hoshen, Jerusalem (IL); Gila Lithwick Yanai, Jerusalem (IL); Ram Eitan, Einat (IL)

(73) Assignees: ROSETTA GENOMICS LTD., Rehovot (IL); MOR RESEARCH APPLICATIONS, Tel Aviv (IL)

( * ) Notice: Subject to any disclaimer, the term of this patent is extended or adjusted under 35 U.S.C. 154(b) by 0 days. days.

(21) Appl. No.: 15/363,822

(22) Filed: Nov. 29, 2016

(65) Prior Publication Data

US 2017/0073775 A1   Mar. 16, 2017

Related U.S. Application Data

(62) Division of application No. 12/999,201, filed as application No. PCT/IL2009/000497 on May 19, 2009, now Pat. No. 9,540,695.

(60) Provisional application No. 61/108,556, filed on Oct. 27, 2008, provisional application No. 61/073,036, filed on Jun. 17, 2008.

(51) Int. Cl.
*C12Q 1/68* (2018.01)
*A61K 31/713* (2006.01)
*A61K 45/00* (2006.01)

(52) U.S. Cl.
CPC .......... *C12Q 1/6886* (2013.01); *A61K 31/713* (2013.01); *A61K 45/00* (2013.01); *C12Q 2600/106* (2013.01); *C12Q 2600/112* (2013.01); *C12Q 2600/118* (2013.01); *C12Q 2600/16* (2013.01); *C12Q 2600/178* (2013.01)

(58) Field of Classification Search
None
See application file for complete search history.

(56) References Cited

U.S. PATENT DOCUMENTS

| | | |
|---|---|---|
| 5,474,796 A | 12/1995 | Brennan |
| 7,683,036 B2 | 3/2010 | Esau et al. |
| 2001/0051344 A1 | 12/2001 | Shalon et al. |
| 2006/0292616 A1 | 12/2006 | Neely |
| 2007/0065844 A1 | 3/2007 | Golub et al. |
| 2007/0178458 A1 | 8/2007 | O'Brien |
| 2007/0269806 A1 | 11/2007 | Ellis |

FOREIGN PATENT DOCUMENTS

| | | |
|---|---|---|
| WO | 2005078139 A2 | 8/2005 |
| WO | 2005118806 A2 | 12/2005 |
| WO | 2006137941 A2 | 12/2006 |

OTHER PUBLICATIONS

Ason, et al., (PNAS Sep. 26, 2006, vol. 103, p. 143855).
Enard, et al., (Science, 2002, vol. 296, p. 340).
Cobb, et al. (Crit Care Med, 2002, vol. 30, p. 2711).
Lucentini (The Scientist, 2004, vol. 18, p. 20).

*Primary Examiner* — Katherine D Salmon
(74) *Attorney, Agent, or Firm* — Polsinelli, PC; Ron Galant

(57) ABSTRACT

Described herein are compositions and methods for the prediction of the prognosis of ovarian cancer subjects. The present invention further provides methods for distinguishing between histological subtypes of ovarian cancer tumors, and also methods and compositions for the treatment or prevention of ovarian cancer. Specifically the invention relates to microRNA molecules associated with said methods and compositions, as well as various nucleic acid molecules relating thereto or derived therefrom.

7 Claims, 10 Drawing Sheets

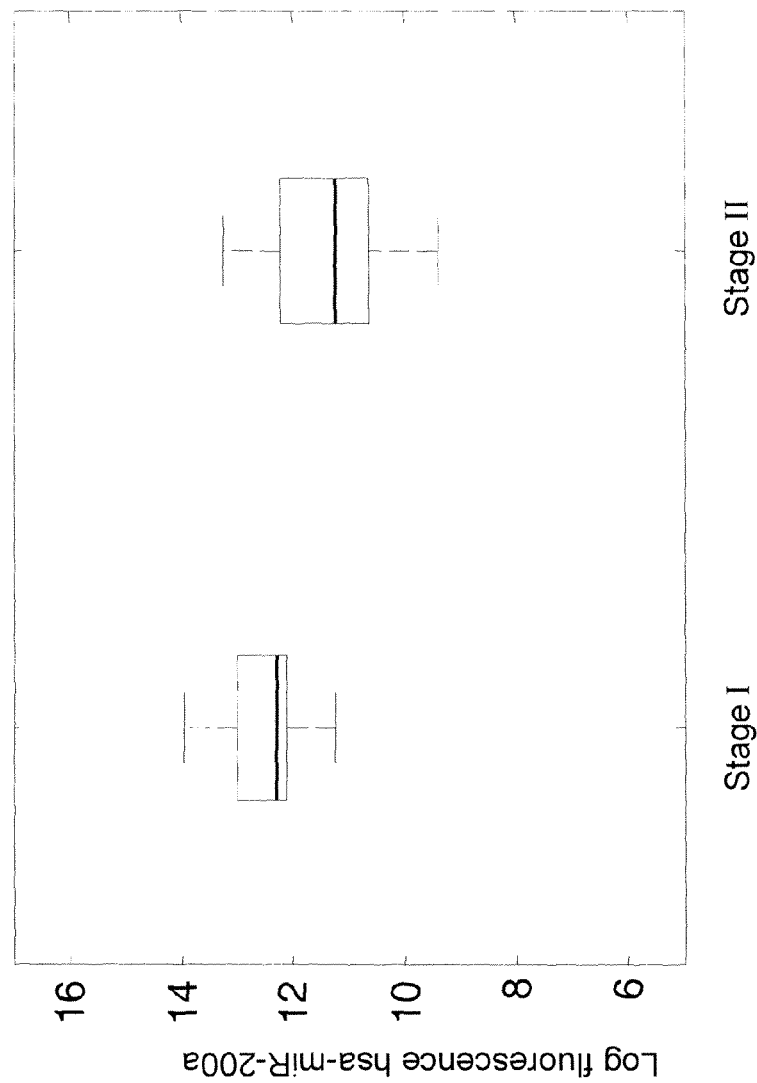

Expression of hsa-let-7i

Expression of hsa-miR-93

COMPOSITIONS AND METHODS FOR PROGNOSIS OF OVARIAN CANCER

CROSS REFERENCE TO RELATED APPLICATIONS

The present application claims priority under 35 U.S.C. § 119(e) to U.S. Provisional Application No. 61/073,036, filed Jun. 17, 2008 and U.S. Provisional Application No. 61/108,556, filed Oct. 27, 2008 which are herein incorporated by reference in their entirety.

FIELD OF THE INVENTION

The invention relates to compositions and methods for the prediction of survival, time to progression, and response to therapy in ovarian cancer subjects. Specifically the invention relates to microRNA molecules associated with the prognosis of ovarian cancer subjects, as well as various nucleic acid molecules relating thereto or derived therefrom.

BACKGROUND OF THE INVENTION

Epithelial ovarian cancer (EOC) is the fifth leading cause of cancer-related deaths in women in the United States and the leading cause of gynecologic cancer related deaths (Jemal A, Siegel et. al, Cancer statistics, 2007, CA Cancer J Clin 2007; 57:43-66). Annually, there are more than 22,000 new cases of ovarian cancer in the United States and over 16,000 deaths. Despite efforts to develop an effective ovarian cancer screening method, most patients still present with advanced (Stages III-IV) disease. Survival of patients diagnosed with ovarian cancer is known to closely correlate with stage at diagnosis.

Treatment for advanced ovarian carcinoma is based on the combination of surgery and chemotherapy. The objective of surgical intervention in patients suffering from advanced disease is to perform cytoreduction to minimal residual disease in the abdominal cavity. Surgery is followed by adjuvant platinum based chemotherapy. The two most important prognostic factors for patients with advanced ovarian carcinoma are the amount of residual disease left after surgery and the response to platinum based chemotherapy.

Platinum-based cytotoxic chemotherapy in conjunction with debulking surgery is currently the gold standard treatment for patients with ovarian cancer. Although 80-90% of patients initially respond to first line treatment, most will either later progress during therapy or recur after complete remission. Patients who have a prolonged disease-free-interval after first line platinum based chemotherapy, are usually rechallenged with platinum and are more likely to respond well to second line therapy. This group of patients has an improved prognosis with a prolonged disease free interval and longer overall survival. Patients who have progressive disease during platinum treatment or who suffer first recurrent disease within a short period of time are termed platinum-resistant. These patients are given alternative chemotherapy regimens who offer relatively small total response rates reaching 20-30% at most. They will usually have a poorer prognosis.

Comparison of the patterns of gene expressions in ovarian cancer and normal ovarian tissue using cDNA micro-arrays revealed several genes that are under- or over-expressed in ovarian cancer (Collins Y, et al. Int J Mol Med 2004; 14:43-53). Patterns of gene expression that predict response to chemotherapeutic agents and prognosis have also been identified.

microRNAs (miRNAs, miRs) are endogenous non-coding small RNAs that interfere with the translation of coding messenger RNAs (mRNAs) in a sequence specific manner, playing a critical role in the control of gene expression during development and tissue homeostasis (Yi et al., 2006, Nat Genet 38, 356-362). Certain miRNAs have been shown to be deregulated in human cancer, and their specific over- or under-expression has been shown to correlate with particular tumor types (Calin and Croce, 2006, Nat Rev Cancer 6, 857-866), as well as to predict patient outcome (Yu et al., 2008, Cancer Cell 13, 48-57). In some cases miRNA overexpression results in reduced expression of tumor suppressor genes, while loss of miRNA expression often leads to oncogene activation.

Thus, there exists a need to identify biomarkers that will make it possible to detect and predict which patients with ovarian cancer will respond to platinum based chemotherapy and which patients will remain refractory to this treatment. Specific data may assist in tailoring treatment to each patient's specific clinical situation during initial management of their disease and also offer the opportunity for better counseling regarding prognosis.

SUMMARY OF THE INVENTION

According to some aspects of the present invention, the expression levels of any of SEQ ID NOS: 1-71 or combination thereof is indicative of survival, time to progression, and response to therapy in ovarian cancer subjects.

The present invention provides a method of determining the prognosis of ovarian cancer in a subject comprising:
(a) obtaining a biological sample from the subject;
(b) determining the expression level in said sample of a nucleic acid sequence selected from the group consisting of SEQ ID NOS: 1-71 and sequences at least about 80% identical thereto; and
(c) comparing said expression level to a threshold expression level,
wherein comparison of said expression level of said nucleic acids to said threshold expression level is predictive of the prognosis of said ovarian-cancer subject.

In one aspect of the invention the prognosis is the prediction of the clinical response of said subject to treatment with a chemotherapeutic agent, and the nucleic acid sequence is selected from the group consisting of SEQ ID NOS: 1-21 and sequences at least about 80% identical thereto. According to one embodiment, an expression level of a nucleic acid sequence selected from the group consisting of SEQ ID NOS: 1-12, 19-21 and sequences at least about 80% identical thereto above said threshold expression level is predictive of resistance to said chemotherapeutic agent. According to another embodiment, an expression level of a nucleic acid sequence selected from the group consisting of SEQ ID NOS: 13-18 and sequences at least about 80% identical thereto above said threshold expression level is predictive of sensitivity to said chemotherapeutic agent. In some embodiments the chemotherapeutic agent is a platinum based agent. In some embodiments the platinum based agent is an agent selected from the group consisting of cisplatin and carboplatin.

In another aspect of the invention, the prognosis is time to progression of the disease in a subject, and the nucleic acids are selected from the group consisting of SEQ ID NOS: 4-7, 19-23, 55 and 71 and sequences at least about 80% identical thereto. According to some embodiments, an expression level of a nucleic acid sequence selected from the group consisting of SEQ ID NOS: 4-7, 19-21, 55 and 71 and sequences at least about 80% identical thereto above said threshold expression level is predictive of short time to progression. According to other embodiments, expression levels of a nucleic acid sequence selected from the group consisting of SEQ ID NO: 22-23 and sequences at least about 80% identical thereto below said threshold expression level is predictive of short time to progression.

According to another aspect of the invention, the prognosis is the prediction of the survival of a subject, and the nucleic acids are selected from the group consisting of SEQ ID NOS: 4-7, 19, 22-23, 55 and 71, and sequences at least about 80% identical thereto. According to some embodiments, an expression level of a nucleic acid sequence selected from the group consisting of SEQ ID NOS: 4-7, 19 and 55 and 71 and sequences at least about 80% identical thereto above said threshold expression level is predictive of short survival. According to other embodiments, expression levels of a nucleic acid sequence selected from the group consisting of SEQ ID NO: 22-23 and sequences at least about 80% identical thereto below said threshold expression level is predictive of short survival.

According to one embodiment of the invention, the biological sample is a tumor tissue at a specific stage. In some embodiments the tumor tissue is at stage III.

According to one embodiment, the biological sample is a tumor tissue of a specific histological subtype. In some embodiments histological subtype is selected from the group consisting of serous papillary cystadenocarcinoma and endometrioid carcinoma.

In another aspect of the invention the prognosis is distinguishing between stage I and stage III of ovarian, cancer, and the nucleic acids are selected from the group consisting of SEQ ID NOS: 22, 23, 30, 31, 36, 38, 40-54, 56-70 and sequences at least about 80% identical thereto. According to some embodiments, expression levels of nucleic acids selected from the group consisting of SEQ ID NOS: 22, 23, 30, 31, 36, 38, 40-44, 56-60 and sequences at least about 80% identical thereto above a threshold expression level is indicative of ovarian cancer stage I. According to other embodiments, expression levels of a nucleic acid sequence selected from the group consisting of SEQ ID NOS: 45-54, 61-70 and sequences at least about 80% identical thereto above a threshold is indicative of ovarian cancer stage III.

The invention further provides a method of distinguishing between papillary serous cystadenocarcinoma and endometrioid carcinoma subtypes of ovarian cancer tumors in a subject comprising:
(a) obtaining a biological sample from said subject;
(b) determining an expression profile in said sample of a nucleic acid sequence selected from the group consisting of SEQ ID NOS: 11-12 and 32-35 and sequences at least about 80% identical thereto; and
(c) comparing said expression profile to a reference expression profile, wherein said comparison is indicative of papillary serous cystadenocarcinoma or endometrioid carcinoma subtype tumor.

According to one embodiment, a relative high expression profile of SEQ ID NOS: 34-35 and sequences at least about 80% identical thereto in said biological sample is indicative of an endometrioid carcinoma subtype tumor. According to another embodiment a relative high expression profile of a nucleic acid selected from the group of 11-12 and 32-33 and sequences at least about 80% identical thereto in said biological sample is indicative of papillary serous cystadenocarcinoma carcinoma subtype tumor.

According to some embodiments, the subject is a human. In some aspects the method is used to determine a course of treatment for the subject.

In some embodiments of the invention the biological sample is selected, from the group consisting of bodily fluid, a cell line and a tissue sample. In some embodiments the tissue is a flesh, frozen, fixed, wax-embedded or formalin fixed paraffin-embedded (FFPE) tissue.

In additional embodiments the expression levels of the invention are determined by a method selected from the group consisting of nucleic acid hybridization, nucleic acid amplification, and a combination thereof. In some embodiments the nucleic acid hybridization is performed using a solid-phase nucleic acid biochip array or in situ hybridization. In some embodiments the real-time PCR method comprises forward and reverse primers, and may further comprise hybridization with a probe comprising a nucleic acid sequence that is complementary to a sequence selected from SEQ ID NOS: 1-71, to a fragment thereof, or to a sequence at least about 80% identical thereto.

The invention further provides a kit for predicting a clinical response of an ovarian cancer subject to treatment with a chemotherapeutic agent, said kit comprising a probe comprising a nucleic acid sequence that is complementary to a sequence selected from SEQ ID NOS: 1-21, to a fragment thereof, or to a sequence at least about 80% identical thereto.

The invention further provides a kit for predicting the time to progression of disease in an ovarian cancer subject, said kit comprising a probe comprising a nucleic acid sequence that is complementary to a sequence selected from SEQ ID NOS: 4-7, 19-23, 55 and 71, to a fragment thereof, or to a sequence at least about 80% identical thereto.

The invention further provides a kit for predicting the survival of an ovarian cancer subject, said kit comprising a probe comprising a nucleic acid sequence that is complementary to a sequence selected from SEQ ID NOS: 4-7, 19-23, 55 and 71, to a fragment thereof, or to a sequence at least about 80% identical thereto.

Further provided is a kit for distinguishing between stage I and stage III of ovarian cancer in a subject, the kit comprising a probe comprising a nucleic acid sequence that is complementary to a sequence selected from SEQ ID NOS: 22, 23, 30, 31, 36, 38, 40-54, 56-70, to a fragment thereof, or to a sequence at least about 80% identical thereto.

Also provided is a kit for distinguishing between papillary serous cystadenocarcinoma and endometrioid subtypes of ovarian cancer tumors in a subject, the kit comprising a probe comprising a nucleic acid sequence that is complementary to a sequence selected from SEQ ID NOS: 11-12 and 32-35, to a fragment thereof, or to a sequence at least about 80% identical thereto.

According to some embodiments the kit of the invention further comprises forward and reverse primers. According to other embodiments the kit comprises reagents for performing in situ hybridization analysis.

Further provided in accordance with the invention is a method of treating or preventing ovarian, cancer in a subject in need thereof comprising administering to the subject an effective amount of a composition comprising a nucleic acid sequence selected from the group consisting of:
(a) SEQ ID NOS: 22-25 and 30-31,
(b) sequences at least about 80% identical to (a),
(c) sequences that are complementary to a sequence selected from the group consisting of SEQ ID NOS: 4-7, 11, 12, 20 and 21; and (d) sequences at least about 80% identical to (c).

An additional aspect of the invention is a use of an effective amount of a composition comprising a nucleic acid sequence selected, from the group consisting of:
(a) SEQ ID NOS: 22-25 and 30-31,
(b) sequences at least about 80% identical to (a),
(c) sequences that are complementary to a sequence selected from the group consisting of SEQ ID NOS: 4-7, 11, 12, 20 and 21; and
(d) sequences at least about 80% identical to (c).
in the preparation of a medicament suitable for administration to a subject for the treatment prevention of ovarian cancer in said subject.

According to some embodiments the composition is suitable for administration in combination with at least one other anticancer agent in unit dosage form. According to some embodiments the anticancer agent is selected from the group consisting of cisplatin, carboplatin, camptothecins, doxorubicin, cyclophosphamide, etoposide, vinblastine, Actinomycin D and cloposide.

BRIEF DESCRIPTION OF THE DRAWINGS

FIGS. 1a-1b show differential expression of microRNAs in ovarian cancers of different stages. Expression scale (Y-axis) shows the logarithm (base 2) of the normalized fluorescence signal by microarray. Boxplots show the median (horizontal line), 25 to 75 percentile (box) and extent of data ("whiskers") for stage I (left box, n=19) and stage III (right box, n=38) patients. FIG. 1a depicts the differential expression for hsa-miR-449b (SEQ m NO: 22, p-value=0.048, median expression 4.6-fold higher in stage I) and FIG. 1b depicts the differential expression for hsa-miR-200a (SEQ ID NO: 30, p-value-0.00047, median expression 2.1-fold higher in stage I).

FIG. 2a presents the differential expression of hsa-miR-27a (SEQ ID NO: 4), with p-value=0.0019 and median expression 1.7-fold higher in resistant patients; FIG. 2b presents the differential expression of hsa-miR-378 (SEQ ID NO: 15), with p-value=0.0055 and median expression 1.8-fold higher in sensitive patients.

In FIGS. 3a-3d each plot presents a curve for each of high (dashed-dotted line, n=13), intermediate (dashed line, n=12) and low (solid line, n=13) tertiles of expression; in FIGS. 3a and 3b for the expression of hsa-miR-23a (SEQ ID NO: 6), and in FIGS. 3c and 3d for the expression of hsa-miR-27a (SEQ ID NO: 4). The X-axis in each of FIGS. 3a-3d depicts survival time, in months; in FIGS. 3a and 3c the Y-axis depicts the fraction of recurrence-free surviving patients, and in FIGS. 3b and 3d the Y-axis depicts the fraction of surviving patients.

DETAILED DESCRIPTION

Figure 1A:
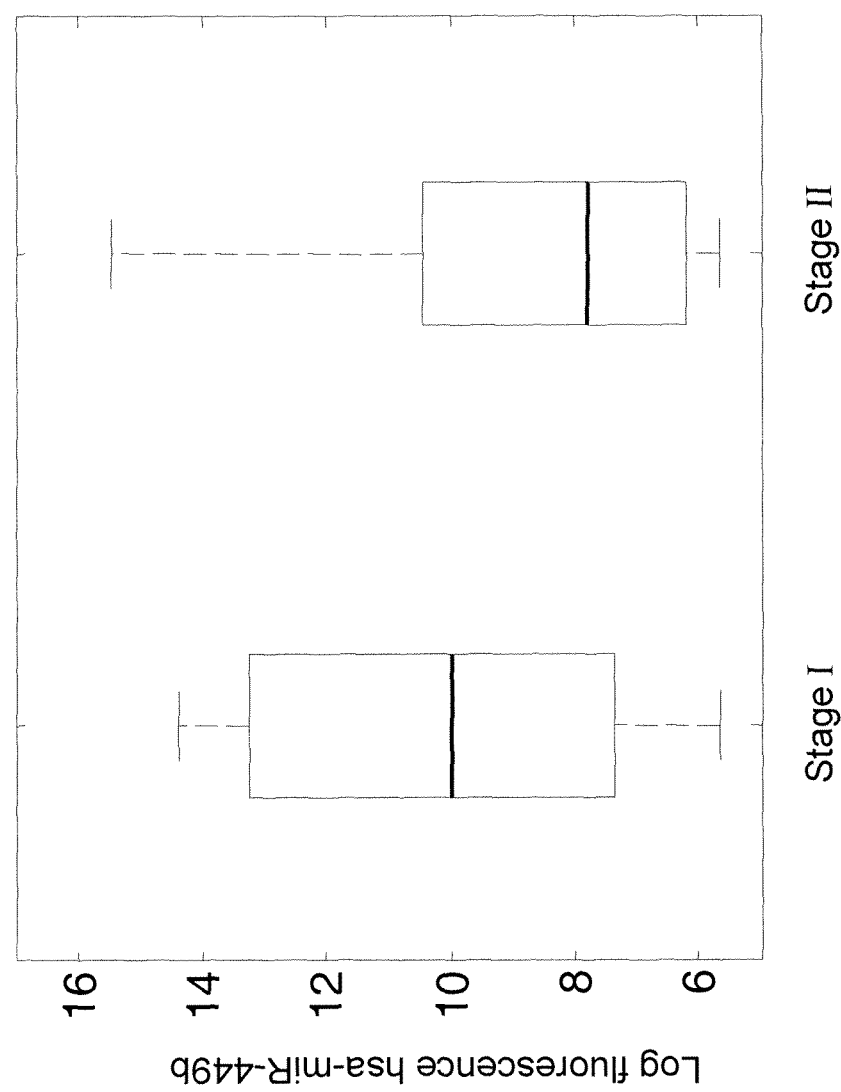

According to some aspects of the present invention miRNA expression can serve as a novel tool for predicting survival, time to progression, and response to therapy in ovarian cancer subjects.

Several miRNAs were significantly differentially expressed between the stage I and stage III ovarian cancers (Table 2). Of particular interest are hsa-miR-200a (SEQ ID NO: 30), hsa-miR-34a (SEQ ID NO: 36), and hsa-miR-449b (SEQ ID NO: 22), which were down-regulated in the advanced (stage III) tumors.

The relation of miRNA expression to the prognosis of ovarian cancer patients was studied. To avoid confounding effects of stage, this analysis was performed in the group of 38 stage III ovarian cancer patients, and two types of analyses were performed which identified several miRNAs. Hsa-miR-378 (SEQ ID NO: 15) was found to have significantly higher expression levels in the groups of patients that were sensitive as compared to resistant to treatment by platinum-based chemotherapy (FIG. 2). Expression of hsa-miR-449b (SEQ ID NO: 22) divided the patients into groups with significantly different disease-specific survival times. Patients with higher expression of hsa-miR-449b were found to have an improved overall survival (Table 4). Hsa-miR-23a (SEQ ID NO: 6) and hsa-miR-27a (SEQ ID NO: 4) were found to be significantly associated with outcome by both methods of analysis. High levels of these miRNAs were associated in both cases with a poorer prognosis.

Many of the ovarian cancer patients who respond completely to first line chemotherapy and are with no evidence of disease at the end of treatment are unfortunately diagnosed with recurrent disease during follow-up. In this study, an array of microRNA markers has been found that are associated with response to platinum-based first line chemotherapy. This approach can potentially be used to tailor chemotherapy to specific patient needs, to help in the selection of the most suitable treatment for those at high risk for recurrence and to better counsel patients on prognosis and the strategies planned to better their outcome. These microRNAs present potential candidates for the development of future therapeutic agents.

Methods and compositions are provided for predicting survival, time to progession, and response to therapy in ovarian cancer subjects. Other aspects of the invention will become apparent to the skilled artisan by the following description of the invention.

Before the present compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

1. Definitions a. Administering

"Administering" means providing a pharmaceutical agent or composition to a subject, and includes, but is not limited to, administering by a medical professional and self-administering.

"Parenteral administration," means administration through injection or infusion. Parenteral administration includes, but is not limited to, subcutaneous administration, intravenous administration, or intramuscular administration.

"Subcutaneous administration" means administration just below the skin.

"Intravenous administration" means administration into a vein.

"Intratumoral administration" means administration within a tumor.

"Chemoembolization" means a procedure in which the blood supply to a tumor is blocked surgically or mechanically and chemotherapeutic agents are administered directly into the tumor.

b. Attached

"Attached" or "immobilized" as used herein to refer to a probe and a solid support may mean that the binding between the probe and the solid support is sufficient to be stable under conditions of binding, washing, analysis, and removal. The binding may be covalent or non-covalent. Covalent bonds may be formed directly between the probe and the solid support or may be formed by a cross linker or by inclusion of a specific reactive group on either the solid support or the probe or both molecules. Non-covalent binding may be one or more of electrostatic, hydrophilic, and hydrophobic interactions. Included in non-covalent binding is the covalent attachment of a molecule, such as streptavidin, to the support and the non-covalent binding of a biotinylated probe to the streptavidin. Immobilization may also involve a combination of covalent and non-covalent interactions.

c. Biological Sample

"Biological sample" as used herein means a sample of biological tissue or fluid that comprises nucleic acids. Such samples include, but are not limited to, tissue or fluid isolated from subjects. Biological samples may also include sections of tissues such as biopsy and autopsy samples, FFPE samples, frozen sections taken for histological purposes, blood, plasma, serum, sputum, stool, tears, mucus, hair, and skin. Biological samples also include explants and primary and/or transformed cell cultures derived from animal or patient tissues.

Biological samples may also be blood, a blood fraction, urine, effusions, ascitic saliva, cerebrospinal fluid, cervical secretions, vaginal secretions, endometrial secretions, gastrointestinal secretions, bronchial secretions, sputum, cell line, tissue sample, cellular content of fine needle aspiration (FNA) or secretions from the breast. A biological sample may be provided by removing a sample of cells from an animal, but can also be accomplished by using previously isolated cells (e.g., isolated by another person, at another time, and/or for another purpose), or by performing the methods described herein in vivo. Archival tissues, such as those having treatment or outcome history, may also be used.

d. Cancer Prognosis

A forecast or prediction of the probable course or outcome of the cancer and response to its treatment. As used herein, cancer prognosis includes distinguishing between cancer stages and subtypes, and the forecast or prediction of any one or more of the following: duration of survival of a patient susceptible to or diagnosed with a cancer, duration of recurrence-free survival, duration of progression free survival of a patient susceptible to or diagnosed with a cancer, response rate in a group of patients susceptible to or diagnosed with a cancer, duration of response in a patient or a group of patients susceptible to or diagnosed with a cancer, and/or likelihood of metastasis in a patient susceptible to or diagnosed with a cancer. As used herein, "prognostic for cancer" means providing a forecast or prediction of the probable course or outcome of the cancer. In some embodiments, "prognostic for cancer" comprises providing the forecast or prediction of (prognostic for) any one or more of the following: duration of survival of a patient susceptible to or diagnosed with a cancer, duration of recurrence-free survival, duration of progression free survival of a patient susceptible to or diagnosed with a cancer, response rate in a group of patients susceptible to or diagnosed with a cancer, duration of response in a patient or a group of patients susceptible to or diagnosed with a cancer, and/or likelihood of metastasis in a patient susceptible to or diagnosed with a cancer.

e. Chemotherapeutic Agent

A drug used to treat a disease, especially cancer. In relation to cancer the drugs typically target rapidly dividing cells, such as cancer cells. Non-limiting examples of chemotherapeutic agents include cisplatin, carboplatin, camptothecins, doxorubicin, cyclophosphamide, paclitaxel, etoposide, vinblastine, Actinomycin D and cloposide.

f. Complement

"Complement" or "complementary" as used herein to refer to a nucleic acid may mean Watson-Crick (e.g., A-T/U and C-G) or Hoogsteen base pairing between nucleotides or nucleotide analogs of nucleic acid molecules. A fill complement or fully complementary may mean 100% complementary base pairing between nucleotides or nucleotide analogs of nucleic acid molecules.

g. Detection

"Detection" means detecting the presence of a component in a sample. Detection also means detecting the absence of a component. Detection also means measuring the level of a component, either quantitatively or qualitatively.

h. Differential Expression

"Differential expression" may mean qualitative or quantitative differences in the temporal and/or cellular gene expression patterns within and among cells and tissue. Thus, a differentially expressed gene can qualitatively have its expression altered, including an activation or inactivation, in, e.g., normal versus disease tissue. Genes may be turned on or turned off in a particular state, relative to another state thus permitting comparison of two or more states. A qualitatively regulated gene will exhibit an expression pattern within a state or cell type that may be detectable by standard techniques. Some genes will be expressed in one state or cell type, but not in both. Alternatively, the difference in expression may be quantitative, e.g., in that expression is modulated, up-regulated, resulting in an increased amount of transcript, or down-regulated, resulting in a decreased amount of transcript. The degree to which expression differs need only be large enough to quantify via standard characterization techniques such as expression arrays, quantitative reverse transcriptase PCR, northern analysis, and RNase protection.

i. Dose

"Dose" as used herein means a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

j. Dosage Unit

"Dosage unit" as used herein means a form in which a pharmaceutical agent is provided. In certain embodiments, a dosage unit is a vial containing lyophilized oligonucleotide. In certain embodiments, a dosage unit is a vial containing reconstituted oligonucleotide.

k. Expression Profile

"Expression profile" as used herein may mean a genomic expression profile, e.g., an expression profile of microRNAs. Profiles may be generated by any convenient means for determining a level of a nucleic acid sequence e.g. quantitative hybridization of microRNA, labeled microRNA, amplified microRNA, cRNA, etc., quantitative PCR, ELISA for quantitation, and the like, and allow the analysis of differential gene expression between two samples. A subject or patient tumor sample, e.g., cells or collections thereof, e.g., tissues, is assayed. Samples are collected by any convenient method, as known in the art. Nucleic acid sequences of interest are nucleic acid sequences that are found to be predictive, including the nucleic acid sequences provided above, where the expression profile may include expression data for 5, 10, 20, 25, 50, 100 or more of, including all of the listed nucleic acid sequences. The term "expression profile" may also mean measuring the abundance of the nucleic acid sequences in the measured samples.

l. FDR

When performing multiple statistical tests, for example in comparing the signal between two groups in multiple data features, there is an increasingly high probability of obtaining false positive results, by random differences between the groups that can reach levels that would otherwise be considered as statistically significant. In order to limit the proportion of such false discoveries, statistical significance is defined only for data features in which the differences reached a p-value (by two-sided t-test) below a threshold, which is dependent on the number of tests performed and the distribution of p-values obtained in these tests.

m. Gene

"Gene" used herein may be a natural (e.g., genomic) or synthetic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA or antisense RNA. A gene may also be an mRNA or cDNA corresponding to the coding regions (e.g., exons and miRNA) optionally comprising 5'- or 3'-untranslated sequences linked thereto. A gene may also be an amplified nucleic acid molecule produced in vitro comprising all or a part of the coding region and/or 5'- or 3'-untranslated sequences linked thereto.

n. Identity

"Identical" or "identity" as used herein in the context of two or more nucleic acids or polypeptide sequences may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

o. Inhibit

"Inhibit" as used herein may mean prevent, suppress, repress, reduce or eliminate.

p. Label

"Label" as used herein may mean a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and other entities which can be made detectable. A label may be incorporated into nucleic acids and proteins at any position.

q. Metastasis

"Metastasis" as used herein means the process by which cancer spreads from the place at which it first arose as a primary tumor to other locations in the body. The metastatic progression of a primary tumor reflects multiple stages, including dissociation from neighboring primary tumor cells, survival in the circulation, and growth in a secondary location.

r. Mismatch

"Mismatch" means a nucleobase of a first nucleic acid that is not capable of pairing with a nucleobase at a corresponding position of a second nucleic acid.

s. Nucleic Acid

"Nucleic acid" or "oligonucleotide" or "polynucleotide" used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

A nucleic acid will generally contain phosphodiester bonds, although nucleic acid analogs may be included that may have at least one different linkage, e.g., phosphoramidate, phosphorothioate, phosphorodithioate, or O-methyl-phosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. The 2'-OH-group may be replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. Modified nucleotides also include nucleotides conjugated with cholesterol through, e.g., a hydroxyprolinol linkage as described in Krutzfeldt et al., Nature 438:685-689 (2005), Soutschek et al., Nature 432:173-178 (2004), and. U.S. Patent Publication No. 20050107325, which are incorporated herein by reference. Additional modified nucleotides and nucleic acids are described in U.S. Patent Publication No. 20050182005, which is incorporated herein by reference. Modifications of the ribose-phosphate backbone may be done for a variety of reasons, e.g., to increase the stability and half-life of such molecules in physiological environments, to enhance diffusion across cell membranes, or as probes on a biochip. The backbone modification may also enhance resistance to degradation, such as in the harsh endocytic environment of cells. The backbone modification may also reduce nucleic acid clearance by hepatocytes, such as in the liver and kidney. Mixtures of naturally occurring nucleic acids and analogs may be made; alternatively, mixtures of different nucleic acid analogs, and mixtures of naturally occurring nucleic acids and analogs may be made.

t. Overall Survival Time

"Overall survival time" or "survival time", as used herein means the time period for which a subject survives after diagnosis of or treatment for a disease. In certain embodiments, the disease is cancer.

u. Progression-Free Survival

"Progression-free survival" means the time period for which a subject having a disease survives, without the disease getting worse. In certain embodiments, progression-free survival is assessed by staging or scoring the disease. In certain embodiments, progression-free survival of a subject having cancer is assessed by evaluating tumor size, tumor number, and/or metastasis.

v. Probe

"Probe" as used herein may mean an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids described herein. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind.

w. Promoter

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

x. Reference Expression Profile

As used herein, the phrase "reference expression profile" refers to a criterion expression value to which measured values are compared in order to determine the detection of a subject with a specific ovarian cancer sub-type. The reference expression profile may be based on the expression of the nucleic acids, or may be based on a combined metric score thereof.

y. Selectable Marker

"Selectable marker" as used herein means any gene which confers a phenotype on a host cell in which it is expressed to facilitate the identification and/or selection of cells which are transfected or transformed with a genetic construct. Representative examples of selectable markers include the ampicillin-resistance gene ($Amp^r$), tetracycline-resistance gene ($Tc^r$), bacterial kanamycin-resistance gene ($Kan^r$), zeocin resistance gene, the AURI-C gene which confers resistance to the antibiotic aureobasidin A, phosphinothricin-resistance gene, neomycin phosphotransferase gene (nptII), hygromycin-resistance gene, beta-glucuronidase (GUS)

gene, chloramphenicol acetyltransferase (CAT) gene, green fluorescent protein (GFP)-encoding gene and luciferase gene.

z. Stringent Hybridization Conditions

"Stringent hybridization conditions" used herein may mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

aa. Substantially Complementary

"Substantially complementary" used herein may mean that a first sequence is at least 60%-99% identical to the complement of a second sequence over a region of 8-50 or more nucleotides, or that the two sequences hybridize under stringent hybridization conditions.

bb. Substantially Identical

"Substantially identical" used herein may mean that a first and second sequence are at least 60%-99% identical over a region of 8-50 or more nucleotides or amino acids, or with respect to nucleic acids, if the first sequence is substantially complementary to the complement of the second sequence.

cc. Subject

As used herein, the term "subject" refers to a mammal, including both human and other mammals. The methods of the present invention are preferably applied to human subjects.

dd. Threshold Expression Level

As used herein, the phrase "threshold expression level" refers to a reference expression value. Measured values are compared to a corresponding threshold expression level to determine the prognosis of a subject.

ee. Therapeutically Effective Amount

"Therapeutically effective amount" or "therapeutically efficient" used herein as to a drug dosage, refer to dosage that provides the specific pharmacological response for which the drug is administered in a significant number of subjects in need of such treatment. The "therapeutically effective amount" may vary according, for example, the physical condition of the patient, the age of the patient and the severity of the disease.

ff. Therapy

"Therapy" as used herein means a disease treatment method. In certain embodiments, therapy includes, but is not limited to, chemotherapy, surgical resection, transplant, and/or chemoembolization.

gg. Treat

"Treat" or "treating" used herein when referring to protection of a subject from a condition may mean preventing, suppressing, repressing, or eliminating the condition. Preventing the condition involves administering a composition described herein to a subject prior to onset of the condition. Suppressing the condition involves administering the composition to a subject after induction of the condition but before its clinical appearance. Repressing the condition involves administering the composition to a subject after clinical appearance of the condition such that the condition is reduced or prevented from worsening. Elimination of the condition involves administering the composition to a subject after clinical appearance of the condition such that the subject no longer suffers from the condition.

hh. Unit Dosage Form

"Unit dosage form," used herein may refer to a physically discrete unit suitable as a unitary dosage for a human or animal subject. Each unit may contain a predetermined quantity of a composition described herein, calculated in an amount sufficient to produce a desired effect in association with a pharmaceutically acceptable diluent, carrier or vehicle. The specifications for a unit dosage form may depend on the particular composition employed and the effect to be achieved, and the pharmacodynamics associated with the composition in the host.

ii. Variant

"Variant" used herein to refer to a nucleic acid may mean (i) a portion of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

jj. Vector

"Vector" used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

2. Treatment of Ovarian Cancer, its Stages, and Histological Subtypes

The treatment of ovarian cancer is based on the stage of the disease which is a reflection of the extent or spread of the cancer to other parts of the body. Staging is performed when the ovarian cancer is removed. During the surgical procedure biopsies are obtained from various sites in the abdominal cavity. During this procedure, depending on the stage of the disease, the surgeon will either remove just the ovary and fallopian tube or will remove ovaries, fallopian tubes and uterus. In addition, the surgeon will attempt to remove as much of the cancer as possible. Ovarian cancer is staged as follows:

Stage I cancer is confined to one or both ovaries. The cancer is Stage II if either one or both of the ovaries is involved and has spread to the uterus and/or the fallopian rubes or other sites in the pelvis. The cancer is Stage III cancer if one or both of the ovaries is involved and has spread to lymph nodes or other sites outside of the pelvis but is still within the abdominal cavity, such as the surface of the intestine or liver. The cancer is Stage IV cancer if one or both ovaries are involved and the cancer has spread outside the abdomen or to the inside of the liver.

The primary treatment of ovarian cancer is surgery at which time the cancer is removed from the ovary and from as many other sites as is possible. Chemotherapy is the second treatment modality. Another treatment modality is radiation, which is used in only certain instances. The treatment of ovarian cancer depends on the stage of the disease, the histological cell type, and the patient's age and overall condition. The histological cell type and the extent of disease based on the biopsies performed during surgery.

Over 75% of ovarian cancers cases are diagnosed at an advanced stage. Overall 5-year survival in ovarian epithelial carcinoma is low because of the preponderance of late-stage disease at diagnosis. The overall 5-year survival rate, according to stages, is:
a. Stage I and II: 80-100%
b. Stage III: 15-20%
c. Stage IV: 5%

Ovarian cancer is classified according to the histology of the tumor. Histology dictates many aspects of clinical treatment, management, and prognosis. Surface epithelial-stromal tumor, also known as ovarian epithelial carcinoma, is the most common type of ovarian cancer. It includes serous tumor (including serous papillary cystadenocarcinoma), endometrioid tumor and mucinous cystadenocarcinoma.

3. MicroRNAs and their Processing

A gene coding for a miRNA may be transcribed leading to production of a miRNA precursor known as the pri-miRNA. The pri-miRNA may be part of a polycistronic RNA comprising multiple pri-miRNAs. The pri-miRNA may form a hairpin with a stem and loop. The stem may comprise mismatched bases.

The hairpin structure of the pri-miRNA may be recognized by Drosha, which is an RNase III endonuclease. Drosha may recognize terminal loops in the pri-miRNA and cleave approximately two helical turns into the stem to produce a 30-200 nt precursor known as the pre-miRNA. Drosha may cleave the pri-miRNA with a staggered cut typical of Rnase III endonucleases yielding a pre-miRNA stem loop with a 5' phosphate and ~2 nucleotide 3' overhang. Approximately one helical turn of stem (~10 nucleotides) extending beyond the Drosha cleavage site may be essential for efficient processing. The pre-miRNA may then be actively transported from the nucleus to the cytoplasm by Ran-GTP and the export receptor Ex-portin-5.

The pre-miRNA may be recognized by Dicer, which is also an Rnase III endonuclease. Dicer may recognize the double-stranded stem of the pre-miRNA. Dicer may also recognize the 5' phosphate and 3' overhang at the base of the stein loop. Dicer may cleave off the terminal loop two helical turns away from the base of the stem loop leaving an additional 5° phosphate and nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. MiRNA* sequences may be found in libraries of cloned miRNAs but typically at lower frequency than miRNAs.

Although initially present as a double-stranded species with mRNA*, the miRNA may eventually become incorporated as a single-stranded RNA into a ribonucleoprotein complex known as the RNA-induced silencing complex (RISC). Various proteins can, form the RISC, which can lead to variability in specifity for miRNA/miRNA* duplexes, binding site of the target gene, activity of miRNA (repress or activate), and which strand of the miRNA/miRNA* duplex is loaded in to the RISC.

When the miRNA strand of the miRNA:miRNA* duplex is loaded into the RISC, the miRNA* may be removed and degraded. The strand of the miRNA:miRNA* duplex that is loaded into the RISC may be the strand whose 5' end is less tightly paired. In cases where both ends of the miRNA:miRNA* have roughly equivalent 5' pairing, both miRNA and miRNA* may have gene silencing activity.

The RISC may identify target nucleic acids based on high levels of complementarity between the miRNA and the mRNA, especially by nucleotides 2-8 of the miRNA. Only one case has been reported in animals where the interaction between the miRNA and its target was along the entire length of the miRNA. This was shown for miR-196 and Hox B8 and it was further shown that miR-196 mediates the cleavage of the Hox B8 mRNA (Yekta et al 2004, Science 304-594). Otherwise, such interactions are known only in plants (Bartel & Bartel 2003, Plant Physiol 132-709).

A number of studies have looked at the base-pairing requirement between miRNA and its mRNA target for achieving efficient inhibition of translation (reviewed by Bartel 2004, Cell 116-281). In mammalian cells, the first 8 nucleotides of the miRNA may be important (Doench & Sharp 2004 GenesDev 2004-504). However, other parts of the microRNA may also participate in mRNA binding. Moreover, sufficient base pairing at the 3' can compensate for insufficient pairing at the 5' (Brennecke et al, 2005 PloS 3-e85). Computation studies, analyzing miRNA binding on whole genomes have suggested a specific role for bases 2-7 at the 5' of the miRNA in target binding but the role of the first nucleotide, found usually to be "A" was also recognized (Lewis et at 2005 Cell 120-15). Similarly, nucleotides 1-7 or 2-8, the "seed", were used to identify and validate targets. MiRNAs differ in their basic structure and sequence of nucleotides; however similarity in seed sequence may suggest similar activity.

The target sites in the mRNA may be in the 5' UTR, the 3° UTR or in the coding region. Interestingly, multiple miRNAs may regulate the same mRNA target by recognizing the same or multiple sites. The presence of multiple miRNA binding sites in most genetically identified targets may indicate that the cooperative action of multiple RISCs provides the most efficient translational inhibition.

miRNAs may direct the RISC to downregulate gene expression by either of two mechanisms: mRNA cleavage or translational repression. The miRNA may specify cleavage of the mRNA if the mRNA has a certain degree of complementarity to the miRNA. When a miRNA guides cleavage, the cut may be between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity between the miRNA and binding site.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

2. Nucleic Acids

Nucleic acids are provided herein. The nucleic acid may comprise the sequence of SEQ ID NOS: 1-71 presented in table 1 or variants thereof. The variant may be a complement of the referenced nucleotide sequence. The variant may also be a nucleotide sequence that is substantially identical to the referenced nucleotide sequence or the complement thereof. The variant may also be a nucleotide sequence which hybridizes under stringent conditions to the referenced nucleotide sequence, complements thereof, or nucleotide sequences substantially identical thereto.

The nucleic acid may have a length of from 10 to 250 nucleotides. The nucleic acid may have a length of at least 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 125, 150, 175, 200 or 250 nucleotides. The nucleic acid may be synthesized or expressed in a cell (in vitro or in vivo) using a synthetic gene described herein. The nucleic acid may be synthesized as a single strand molecule and hybridized to a substantially complementary nucleic acid to form a duplex. The nucleic acid may be introduced to a cell, tissue or organ in a single- or double-stranded form or capable of being expressed by a synthetic gene using methods well known to those skilled in the art, including as described in U.S. Pat. No. 6,506,559 which is incorporated by reference.

TABLE 1

| miR name* | miR SEQ ID NO: | Hairpin SEQ ID NO: |
| --- | --- | --- |
| hsa-miR-199a-3p | 1 | 2, 3 |
| hsa-miR-27a | 4 | 5 |
| hsa-miR-23a | 6 | 7 |
| hsa-miR-30c | 8 | 9, 10 |
| hsa-let-7g | 11 | 12 |
| MID-00689 | 13 | 14 |
| hsa-miR-378 | 15 | 16 |
| hsa-miR-625 | 17 | 18 |
| hsa-miR-23a* | 19 | 7 |
| hsa-miR-21 | 20 | 21 |
| hsa-miR-449b | 22 | 23 |
| hsa-miR-449a | 24 | 25 |
| hsa-miR-34c-5p | 28 | 29 |
| hsa-miR-200a | 30 | 31 |
| hsa-let-7i | 32 | 33 |
| hsa-miR-93 | 34 | 35 |
| hsa-miR-34a | 36 | 38 |
| hsa-miR-34b* | 37 | 39 |
| hsa-miR-200b | 40 | 56 |
| hsa-miR-513a-5p | 41 | 57 |
| hsa-miR-509-3p | 42 | 58 |
| hsa-miR-509-3-5p | 43 | 59 |
| hsa-miR-574-5p | 44 | 60 |
| hsa-miR-423-3p | 45 | 61 |
| hsa-miR-130a | 46 | 62 |
| hsa-miR-146b-5p | 47 | 63 |
| hsa-miR-193a-3p | 48 | 64 |
| hsa-miR-193a-5p | 49 | 65 |
| hsa-miR-491-5p | 50 | 66 |
| hsa-miR-23b | 51 | 67 |
| hsa-miR-125a-3p | 52 | 68 |
| hsa-miR-125a-5p | 53 | 69 |
| hsa-miR-451 | 54 | 70 |
| hsa-miR-24-2* | 55 | 71 |

*MID-00689 was cloned at Rosetta Genomics. For all the other sequences the miR name is the miRBase registry name (release 10).

a. Nucleic Acid Complex

The nucleic acid may further comprise one or more of the following: a peptide, a protein, a RNA-DNA hybrid, an antibody, an antibody fragment, a Fab fragment, and an aptamer. The nucleic acid may also comprise a protamine-antibody fusion protein as described in Song et al (Nature Biotechnology 2005; 23:709-17) and Rossi (Nature Biotechnology 2005: 23; 682-4), the contents of which are incorporated herein by reference. The protamine-fusion protein may comprise the abundant and highly basic cellular protein protamine. The protamine may readily interact with the nucleic acid. The protamine may comprise the entire 51 amino acid protamine peptide or a fragment thereof. The protamine may be covalently attached to another protein, which may be a Fab. The Fab may bind to a receptor expressed on a cell surface.

b. Pri-miRNA

The nucleic acid may comprise a sequence of a pri-miRNA or a variant thereof. The pri-miRNA sequence may comprise from 45-30,000, 50-25,000, 100-20,000, 1,000-1,500 or 80-100 nucleotides. The sequence of the pri-miRNA may comprise a pre-miRNA, miRNA and miRNA*, as set forth herein, and variants thereof. The sequence of the pri-miRNA may comprise the sequence of SEQ ID NOS: 1-71 or variants thereof.

The pri-miRNA may form a hairpin structure. The hairpin may comprise first and second nucleic acid sequence that are substantially complimentary. The first and second nucleic acid sequence may be from 37-50 nucleotides. The first and second nucleic acid sequence may be separated by a third sequence of from 8-12 nucleotides. The hairpin structure may have a free energy less than −25 Kcal/mole as calculated by the Vienna algorithm with default parameters, as described in Hofacker et al., Monatshefte f. Chemie 125: 167-188 (1994), the contents of which are incorporated herein. The hairpin may comprise a terminal loop of 4-20, 8-12 or 10 nucleotides. The pri-miRNA may comprise at least 19% adenosine nucleotides, at least 16% cytosine nucleotides, at least 23% thymine nucleotides and at least 19% guanine nucleotides.

c. Pre-miRNA

The nucleic acid may also comprise a sequence of a pre-miRNA or a variant thereof. The pre-miRNA sequence may comprise from 45-200, 60-80 or 60-70 nucleotides. The sequence of the pre-miRNA may comprise a miRNA and a miRNA* as set forth herein. The sequence of the pre-miRNA may also be that of a pri-miRNA excluding from 0-160 nucleotides from the 5' and 3' ends of the pri-miRNA. The sequence of the pre-miRNA may comprise the sequence of SEQ ID NOS: 1-71 or variants thereof.

d. MiRNA

The nucleic acid may also comprise a sequence of a miRNA (including miRNA*) or a variant thereof. The miRNA sequence may comprise from 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA, may also be the last 13-33 nucleotides of the pre-miRNA. The sequence of the miRNA may comprise the sequence of SEQ ID NOS: 1, 4, 6, 8, 11, 13, 15, 17, 19, 20, 22, 24, 28, 30 and 34, 36, 37 and 40-55, or variants thereof.

e. Anti-miRNA

The nucleic acid may also comprise a sequence of an anti-miRNA that is capable of blocking the activity of a miRNA or miRNA*, such as by binding to the pri-miRNA, pre-miRNA, miRNA or miRNA* (e.g. antisense or RNA silencing), or by binding to the target binding site. The anti-miRNA may comprise a total of 5-100 or 10-60 nucleotides. The anti-miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the anti-miRNA may comprise (a) at least 5 nucleotides that are substantially identical or complimentary to the 5' of a miRNA and at least 5-12 nucleotides that are substantially complimentary to the flanking regions of the target site from the 5' end of the miRNA, or (b) at least 5-12 nucleotides that are substantially identical or complimentary to the 3' of a miRNA and at least 5 nucleotide that are substantially complimentary to the flanking region of the target site from the 3' end of the miRNA. The sequence of the anti-miRNA may comprise the compliment of SEQ ID NOS: 1, 4, 6, 8, 11, 13, 15, 17, 19, 20, 22, 24, 28, 30 and 34, 36, 37 and 40-55, or variants thereof.

5. Probes

A probe is also provided comprising a nucleic acid described herein. Probes may be used for screening and diagnostic methods. The probe may be attached or immobilized to a solid substrate, such as a biochip.

The probe may have a length of from 8 to 500, 10 to 100 or 20 to 60 nucleotides. The probe may also have a length of at least 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 220, 240, 260, 280 or 300 nucleotides. The probe may further comprise a linker sequence of from 10-60 nucleotides.

6. Biochip

A biochip is also provided. The biochip may comprise a solid substrate comprising an attached probe or plurality of probes described herein. The probes may be capable of hybridizing to a target sequence under stringent hybridization conditions. The probes may be attached at spatially defined address on the substrate. More than one probe per target sequence may be used, with either overlapping probes or probes to different sections of a particular target sequence. The probes may be capable of hybridizing to target sequences associated with a single disorder appreciated by those in the art. The probes may either be synthesized first, with subsequent attachment to the biochip, or may be directly synthesized on the biochip.

The solid substrate may be a material that may be modified to contain discrete individual sites appropriate for the attachment or association of the probes and is amenable to at least one detection method. Representative examples of substrates include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. The substrates may allow optical detection without appreciably fluorescing.

The substrate may be planar, although other configurations of substrates may be used as well. For example, probes may be placed on the inside surface of a tube, for flow-through sample analysis to minimize sample volume. Similarly, the substrate may be flexible, such as a flexible foam, including closed cell foams made of particular plastics.

The biochip and the probe may be derivatized with chemical functional groups for subsequent attachment of the two. For example, the biochip may be derivatized with a chemical functional group including, but not limited to, amino groups, carboxyl groups, oxo groups or thiol groups. Using these functional groups, the probes may be attached using functional groups on the probes either directly or indirectly using a linker. The probes may be attached to the solid support by either the 5' terminus, 3' terminus, or via an internal nucleotide.

The probe may also be attached to the solid support non-covalently. For example, biotinylated oligonucleotides can be made, which may bind to surfaces covalently coated with streptavidin, resulting in attachment. Alternatively, probes may be synthesized on the surface using techniques such as photopolymerization and photolithography.

7. Therapeutic

A method for treating a disease or disorder associated with ovarian cancer is also provided. Furthermore, existing miRNA molecules may be used as starting materials for the manufacture of sequence-modified miRNA molecules. Further, miRNA molecules may be modified, in order that they are processed and then generated as double-stranded siRNAs which are again directed against therapeutically relevant targets.

As previously discussed the methods, compositions and articles of manufacture of the present invention are particularly useful in the treatment of cancer.

The compositions of the present invention may be combined with a chemotherapeutic agent, a combination of chemotherapeutic agents and/or radiotherapy.

Cancer treatments often comprise more than one therapy. As such, in certain embodiments the present invention provides methods for treating cancer comprising administering to a subject in need thereof the composition of the present invention, and further comprising administering at least one additional therapy.

In certain embodiments, an additional therapy may also be designed to treat cancer. An additional therapy may be a chemotherapeutic agent. Suitable chemotherapeutic agents include 5-fluorouracil, gemcitabine, doxorubicine, mitomycin c, sorafenib, etoposide, carboplatin, epirubicin, irinotecan and oxaliplatin. An additional therapy may be surgical resection of tumor(s), or chemoembolization.

8. Diagnostic

A method of diagnosis is also provided. The method comprises detecting a differential expression level of a disease-associated nucleic acid in a biological sample. The sample may be derived from a patient. Diagnosis of a disease state in a patient may allow for prognosis and selection of therapeutic strategy. Further, the developmental stage of cells may be classified by determining temporarily expressed disease-associated nucleic acids.

In situ hybridization of labeled probes to tissue arrays may be performed. When comparing the fingerprints between an individual and a standard, the skilled artisan can make a diagnosis, a prognosis, or a prediction based on the findings. It is further understood that the nucleic acids which indicate the diagnosis may differ from those which indicate the prognosis and molecular profiling of the condition of the cells may lead to distinctions between responsive or refractory conditions or may be predictive of outcomes.

9. Kits

A kit is also provided and may comprise a nucleic acid described herein together with any or all of the following:

assay reagents, buffers, probes and/or primers, and sterile saline or another pharmaceutically acceptable emulsion and suspension base. In addition, the kits may include instructional materials containing directions (e.g., protocols) for the practice of the methods described, herein.

For example, the kit may be a kit for the amplification, detection, identification or quantification of a target nucleic acid sequence. The kit may comprise a poly(T) primer, a forward primer, a reverse primer, and a probe.

10. Compositions

A pharmaceutical composition is also provided. The composition may comprise a nucleic acid described herein and optionally a pharmaceutically acceptable carrier. The composition may encompass modified oligonucleotides that are identical, substantially identical, substantially complementary or complementary to any nucleobase sequence version of the miRNAs or nucleic acids described herein or a precursor thereof.

The compositions may be used for therapeutic applications. The pharmaceutical composition may be administered by known methods, including wherein a nucleic acid is introduced into a desired target cell in vitro or in vivo.

Methods for the delivery of nucleic acid molecules are described in Akhtar et al. (Trends Cell Bio. 2, 139, 1992). WO 94/02595 describes general methods for delivery of RNA molecules. These protocols can be utilized for the delivery of virtually any nucleic acid molecule. Nucleic acid molecules can be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. Alternatively, the nucleic acid/vehicle combination is locally delivered by direct injection or by use of an infusion pump. Other routes of delivery include, but are not limited to oral (tablet or pill form) and/or intrathecal delivery (Gold, 1997, Neuroscience, 76, 1153-1158). Other approaches include the use of various transport and carrier systems, for example, through the use of conjugates and biodegradable polymers. More detailed descriptions of nucleic acid delivery and administration are provided for example in WO93/23569, WO99/05094, and WO99/04819.

The nucleic acids can be introduced into tissues or host cells by any number of routes, including viral infection, microinjection, or fusion of vesicles. Jet injection may also be used for intra-muscular administration, as described by Furth et al. (Anal Biochem 115 205:365-368, 1992). The nucleic acids can be coated onto gold microparticles, and delivered intradermally by a particle bombardment device, or "gene gun" as described in the literature (see, for example, Tang et al. Nature 356:152-154, 1992), where gold microprojectiles are coated with the DNA, then bombarded into skin cells.

The compositions of the present invention can be formulated into pharmaceutical compositions by combination with appropriate, pharmaceutically acceptable carriers or diluents, and can be formulated into preparations in solid, semi-solid, liquid or gaseous forms, such as tablets, capsules, powders, granules, ointments, solutions, suppositories, injections, inhalants and aerosols. As such, administration of the agents can be achieved in various ways, including oral, buccal, rectal, parenteral, intraperitoneal, intradermal, transdermal, intracheal, etc.

In certain embodiments, a pharmaceutical composition of the present invention is administered in the form of a dosage unit (e.g., tablet, capsule, bolus, etc.). In certain embodiments, such pharmaceutical compositions comprise a modified oligonucleotide in a dose selected from 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 270 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, and 800 mg. In certain such embodiments, a pharmaceutical composition of the present invention comprises a dose of modified oligonucleotide selected from 25 mg, 50 mg, 75 mg, 100 mg, 150 mg, 200 mg, 250 mg, 300 mg, 350 mg, 400 mg, 500 mg, 600 mg, 700 mg, and 800 mg.

In certain embodiments, a pharmaceutical agent is sterile lyophilized modified oligonucleotide that is reconstituted with a suitable diluent, e.g., sterile water for injection or sterile saline for injection. The reconstituted product is administered as a subcutaneous injection or as an intravenous infusion after dilution into saline. The lyophilized drug product consists of a modified oligonucleotide which has been prepared in water for injection, or in saline for injection, adjusted to pH 7.0-9.0 with acid or base during preparation, and then lyophilized. The lyophilized modified oligonucleotide may be 25-800 mg of a modified oligonucleotide. It is understood that this encompasses 25, 50, 75, 100, 125, 150, 175, 200, 225, 250, 275, 300, 325, 350, 375, 425, 450, 475, 500, 525, 550, 575, 600, 625, 650, 675, 700, 725, 750, 775, and 800 mg of modified lyophilized oligonucleotide.

In certain embodiments, the compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation.

In certain embodiments, pharmaceutical compositions of the present invention comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition of the present invention is prepared using known techniques, including, but not limited to mixing, dissolving, granulating, dragee-making, levigating, emulsifying, encapsulating, entrapping or tabletting processes.

In certain embodiments, a pharmaceutical composition of the present invention is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

In certain embodiments, a pharmaceutical composition of the present invention is a solid. (e.g., a powder, tablet, and/or capsule). In certain of such embodiments, a solid pharmaceutical composition comprising one or more oligonucleotides is prepared using ingredients known in the art, including, but not limited to, starches, sugars, diluents, granulating agents, lubricants, binders, and disintegrating agents.

In certain embodiments, a pharmaceutical composition of the present invention is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition of the present invention comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition of the present invention comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition of the present invention comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition of the present invention comprises a sustained-release system. A non-limiting example of such a sustained-release system is a semi-permeable matrix of solid hydrophobic polymers. In certain embodiments, sustained-release systems may, depending on their chemical nature, release pharmaceutical agents over a period of hours, days, weeks or months.

In certain embodiments, a pharmaceutical composition of the present invention is prepared for oral administration. In certain of such embodiments, a pharmaceutical composition is formulated by combining one or more compounds comprising modified oligonucleotides with one or more pharmaceutically acceptable carriers. Certain of such carriers enable pharmaceutical compositions to be formulated as tablets, pills, dragees, capsules, liquids, gels, syrups, slurries, suspensions and the like, for oral ingestion by a subject. In certain embodiments, pharmaceutical compositions for oral use are obtained by mixing oligonucleotide and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added, in certain embodiments, pharmaceutical compositions are formed to obtain tablets or dragee cores. In certain embodiments, disintegrating agents (e.g., cross-linked polyvinyl pyrrolidone, agar, or alginic acid or a salt thereof, such as sodium alginate are added.

In certain embodiments, dragee cores are provided with coatings. In certain such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more pharmaceutical agents of the present invention in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more pharmaceutical agents of the present invention are be dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition is prepared for administration by inhalation. Certain of such pharmaceutical compositions for inhalation are prepared in the form of an aerosol spray in a pressurized pack or a nebulizer. Certain of such pharmaceutical compositions comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a pharmaceutical agent of the invention and a suitable powder base such as lactose or starch.

In certain embodiments, a pharmaceutical composition is prepared for rectal administration, such as a suppositories or retention enema. Certain of such pharmaceutical compositions comprise known ingredients, such as cocoa butter and/or other glycerides.

In certain embodiments, a pharmaceutical composition is prepared for topical administration. Certain of such pharmaceutical compositions comprise bland moisturizing bases, such as ointments or creams. Exemplary suitable ointment bases include, but are not limited to, petrolatum, petrolatum plus volatile silicones, and lanolin and water in oil emulsions. Exemplary suitable cream bases include, but are not limited to, cold cream and hydrophilic ointment.

In certain embodiments, a pharmaceutical composition of the present invention comprises a modified oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotides of the present invention are formulated as a prodrug. In certain embodiments, upon in vivo administration, a prodrug is chemically converted to the biologically, pharmaceutically or therapeutically more active form of a modified oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, a prodrug is produced by modifying a pharmaceutically active compound such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

Having now generally described the invention, the same will be more readily understood through reference to the following examples, which are provided by way of illustration and are not intended to be limiting of the present invention.

EXAMPLES

Example 1: Materials and Methods a. Patients and Samples

Patients, who were surgically treated for ovarian cancer at the Rabin Medical Center between January, 2000 and December, 2004 were identified. All pathology slides were re-evaluated by an expert pathologist. Tumor histology was established and the diagnosis of EOC was confirmed. Only serous papillary and endometrioid histology were included in the study. Patients found to have a synchronous endometrial malignancy were excluded. For each patient, a formalin-fixed paraffin embedded (FFPE) tumor sample was obtained and tumor cell content was evaluated by a pathologist. Only tumor samples with a minimum of 50% tumor tissue content were included. Patient charts were reviewed for clinicopathologic information—demographics, surgical procedure and findings, pathology, chemotherapy regimens and response, follow-up and survival. Optimal surgical cytoreduction was defined during the study period as the largest residual tumor diameter of 1 cm. Patients with progressive disease during first line platinum based chemotherapy or those who suffered recurrent disease within 6 months of completing first line therapy were termed platinum resistant. Patients with no recurrence or with recurrences beyond 6 months were termed platinum sensitive. Survival time was calculated as the time from the end of treatment to the last follow-up date or death. Recurrence time was calculated as the time from the end of treatment to the time of detected recurrence/progression. The study was approved by the institutional review board of the Rabin Medical Center.

Fifty-seven patients were identified to fit study criteria. Nineteen patients had stage disease at diagnosis and 38 patients had stage III at diagnosis. Due to small numbers, stage II and stage IV patients were excluded from the study. One patient was censored after 161 days (due to death of other causes). Median age of the study cohort was 58 years. Of the stage III patients, 18 had optimal surgical cytoreduction and 15 were left with sub-optimal residual disease at the end of surgery. Thirty five patients were diagnosed with serous adenocarcinoma and 22 with endometrioid histology.

Most of the 19 patients with stage I disease were staged according to FIGO guidelines. All of them had bilateral salpingo-oophorectomy (BSO), cytology washings and omentectomy performed; 12 (63%) had lymph-node sampling (LNS); 10 (52%) appendectomy; and 14 (73%) total abdominal hysterectomy (TAR).

All patients received platinum based chemotherapy as first-line treatment. 21 patients received platinum as a single agent, 34 received paclitaxel with carboplatin, and 2 patients received cyclophosphamide with cisplatin.

b. RNA Extraction

For FFPE samples, total RNA was isolated from seven to ten 10-μm-thick tissue sections using the microRNA extraction protocol developed at Rosetta Genomics. Briefly, the sample is incubated a few times in Xylene at 57° to remove paraffin excess, followed by Ethanol washes. Proteins are degraded by proteinase K solution at 45° C. for few hours. The RNA is extracted with acid phenol:chloroform followed by ethanol precipitation and DNAse digestion. Total RNA quantity and quality is checked by spectrophotometer (Nanodrop ND-1000).

From frozen tissues, total RNA was extracted using the miRvana microRNA isolation kit (Ambion).

c. microRNA Microarray Platform

Custom microarrays were produced by printing DNA oligonucleotide probes representing 903 human microRNAs. Each probe, printed in triplicate, carries up to 22-nt linker at the 3' end of the microRNA's complement sequence in addition to an amine group used to couple the probes to coated glass slides. 20 μM of each probe were dissolved in 2×SSC+0.0035% SDS and spotted in triplicate on Schott Nexterion® Slide E coated microarray slides (Mainz, Germany) using a Genomic Solutions® BioRobotics MicroGrid II according the MicroGrid manufacturer's directions. 22 negative control probes were designed using the sense sequences of different microRNAs. Two groups of positive control probes were designed to hybridize to the microarray (i) synthetic small RNA were spiked to the RNA before labeling to verify the labeling efficiency and (ii) probes for abundant small RNA (e.g. small nuclear RNAs (U43, U49, U24, Z30, U6, U48, U44), 5.8 s and 5 s ribosomal RNA) are spotted on the array to verify RNA quality. The slides were blocked in a solution containing 50 mM ethanolamine, 1M Tris (pH9.0) and 0.1% SDS for 20 min at 50° C., then thoroughly rinsed with water and spun dry.

d. Cy-Dye Labeling of MicroRNA for Microarray

Five μg of total RNA were labeled by ligation (Thomson et al., Nature Methods 2004, 1:47-53) of an RNA-linker, p-rCrU-Cy/dye (Dharmacon, Lafayette), to the 3'-end with Cy3 or Cy5. The labeling reaction contained total RNA, spikes (0.1-20 fmoles), 400 ng RNA-linker-dye, 15% DMSO, 1× ligase buffer and 20 units of T4 RNA ligase (NEB) and proceeded at 4° C. for 1 hr followed by 1 hr at 37° C. The labeled. RNA was mixed with 3× hybridization buffer (Ambion), heated to 95° C. for 3 min and then added on top of the microarray. Slides were hybridized 12-16 hr in 42° C., followed by two washes in room temperature with 1×SSC and 0.2% SDS and a final wash with 0.1×SSC.

Arrays were scanned using an Agilent Microarray Scanner Bundle G2565BA (resolution of 10 μm at 100% and 10% power). Array images were analyzed using SpotReader software (Niles Scientific).

e. Data Analysis

Expression levels between groups of samples were compared using the Mann-Whitney non-parametric test. Only microRNAs which had a median signal higher than signal background levels (normalized fluorescence signal of ~300) in at least one of the two groups were tested. Corrections for multiple pairwise comparisons were performed using the Benjamini-Hochberg "False Discovery Rate" (FDR) method. Survival time course was studied using the Kaplan Meier method, and groups were compared using logrank test. Stability of microRNAs in survival analysis was assessed by repeated (100 times) random resampling (bootstrap) from the original dataset (maintaining group sizes). Multivariate analysis of microRNA expression (for hsa-miR-27a), grade, age, optimal cytoreduction, and histological type was performed using Cox regression. The values of these features were combined in order to predict progression times in stage III patients. Histological type was encoded such that endometrioid carcinoma samples were given a value of one, while serous carcinomas were given a value of zero. Similarly, a value of one or zero was assigned for samples with or without optimal cytoreduction, respectively.

f. MicroRNA Target Prediction

Targets were selected from the intersection of the target prediction results by Targetscan and Miranda. Only targets with a Targetscan score lower than 0, a Miranda score>=150 were used. In order to retrieve only the most relevant targets, we listed only genes targeted by at least three microRNAs that we found to be associated with poor prognosis. This list included the microRNAs that were over-expressed in platinum-resistant stage III patients compared to platinum-sensitive stage III patients (including hsa-miR-27a (SEQ ID NO: 4), hsa-miR-23a (SEQ ID NO: 6), hsa-miR-30c (SEQ ID NO: 8), hsa-let-7g (SEQ ID NO: 11), hsa-miR-199a-3p (SEQ ID NO: 1)) and the microRNAs that were associated with significantly poorer recurrence-free survival (including hsa-miR-27a, hsa-miR-23a, hsa-miR-21 (SEQ ID NO: 20)). In addition, since hsa-miR-27a and hsa-miR-23a were significant in both the differential expression analysis and in the progression-free survival analysis, only genes that were targeted by at least one of these two microRNAs were listed.

Example 2: miR Expression Patterns Correlate with Stage of Disease

Time to progression and survival were clearly linked to stage in the study cohort of patients. The microRNA expression were compared between stage I (n=19) and stage III (n=38) cases. 18 microRNAs (Table 2) were differentially expressed with p<0.05 (Mann-Whitney test), including for example hsa-miR-449b (SEQ ID NO: 22) (p=0.048). hsa-miR-200a (SEQ ID NO: 30) (p=0.00047) was also significant when allowing a False Discovery Rate (FDR) of 10%. Both of these microRNAs were more highly expressed in stage I ovarian cancers compared to stage III cases. Fold-change is the ratio of the median signals in the two groups.

TABLE 2

| miR | SEQ ID NO: | p-value | fold-change | higher in |
|---|---|---|---|---|
| hsa-miR-200a | 30 | 0.00047 | 2.10 | Stage I |
| hsa-miR-200b | 40 | 0.0043 | 1.63 | Stage I |
| hsa-miR-34a | 36 | 0.0066 | 1.69 | Stage I |
| hsa-miR-513a-5p | 41 | 0.0068 | 5.32 | Stage I |
| hsa-miR-509-3p | 42 | 0.0074 | 10.3 | Stage I |
| hsa-miR-509-3-5p | 43 | 0.017 | 4.01 | Stage I |
| hsa-miR-574-5p | 44 | 0.045 | 1.24 | Stage I |
| hsa-miR-449b | 22 | 0.048 | 4.61 | Stage I |
| hsa-miR-423-3p | 45 | 0.0024 | 1.33 | Stage III |
| hsa-miR-130a | 46 | 0.0033 | 1.86 | Stage III |
| hsa-miR-146b-5p | 47 | 0.0037 | 2.27 | Stage III |
| hsa-miR-193a-3p | 48 | 0.0056 | 1.42 | Stage III |
| hsa-miR-193a-5p | 49 | 0.013 | 1.60 | Stage III |
| hsa-miR-491-5p | 50 | 0.028 | 1.40 | Stage III |
| hsa-miR-23b | 51 | 0.028 | 1.10 | Stage III |
| hsa-miR-125a-3p | 52 | 0.030 | 1.27 | Stage III |
| hsa-miR-125a-5p | 53 | 0.034 | 1.25 | Stage III |
| hsa-miR-451 | 54 | 0.035 | 1.93 | Stage III |

The boxplots in FIGS. 1a-1b exemplify the differential expression for hsa-miR-449b (SEQ ID NO: 22, FIG. 1a) and hsa-miR-200a (SEQ ID NO: 30, FIG. 1b) such that the expression levels of both these miRs are higher in stage I tumors than in stage III tumors of ovarian cancer.

Accordingly, relatively high expressions of any of hsa-miR-200a (SEQ ID NO: 30), hsa-miR-200b (SEQ ID NO: 40), hsa-miR-34a (SEQ ID NO: 36), hsa-miR-513a-5p (SEQ ID NO: 41), hsa-miR-509-3p (SEQ ID NO: 42), hsa-miR-509-3-5p (SEQ ID NO: 43), hsa-miR-574-5p (SEQ ID NO: 44) and hsa-miR-449b (SEQ ID NO: 22) are indicative of stage I tumors of ovarian cancer, and relatively high expressions of any of hsa-miR-423-3p (SEQ ID NO: 45), hsa-miR-130a (SEQ ID NO: 46), hsa-miR-146b-5p (SEQ ID NO: 47), hsa-miR-193a-3p (SEQ ID NO: 48), hsa-miR-193a-5p (SEQ ID NO: 49), hsa-miR-491-5p (SEQ ID NO: 50), hsa-miR-23b (SEQ ID NO: 51), hsa-miR-125a-3p (SEQ ID NO: 52), hsa-miR-125a-5p (SEQ ID NO: 53) and hsa-miR-451 (SEQ ID NO: 54) are indicative of stage III tumors of ovarian cancer.

Example 3: miR Expression Patterns in Patients with Stage III Disease Correlate with Response to Platinum Therapy The relation between miR expression and disease progression was studied. Since patient prognosis and disease characteristics vary for different stages of the disease, the inventors focused on the larger, higher risk group of patients in stage III. 25 patients achieved a complete response with no recurrence within 6 months of the end of treatment, and were termed platinum-sensitive. Twelve patients had rapid progression of the disease (partial response or recurrence within 6 months of the end of treatment) and were termed platinum-resistant. The patient censored before 6 months was not included in this analysis.

miR expression patterns were examined in tumors from platinum-resistant stage III patients (n=12) and in tumors from platinum-sensitive stage III patients (n=25). As shown in table 3, hsa-miR-199a-3p (SEQ ID NO: 1), hsa-miR-27a (SEQ II) NO: 4), hsa-miR-23a (SEQ ID NO: 6), hsa-miR-30c (SEQ ID NO: 8), hsa-let-7g (SEQ ID NO: 11), MID-00689 (SEQ ID NO: 13), hsa-miR-23a* (SEQ ID NO: 19), hsa-miR-21 (SEQ ID NO: 20), hsa-miR-378 (SEQ ID NO: 15), and hsa-miR-625 (SEQ ID NO: 17) were found to be significantly differentially expressed in tumors from platinum sensitive vs. platinum resistant patients (p-value<0.05).

TABLE 3

| miR | SEQ ID NO: | p-value | fold-change | higher in |
|---|---|---|---|---|
| hsa-miR-199a-3p | 1 | 0.046 | 2.32 | resistant |
| hsa-miR-27a | 4 | 0.0019 | 1.67 | resistant |
| hsa-miR-23a | 6 | 0.011 | 1.44 | resistant |
| hsa-miR-30c | 8 | 0.029 | 1.41 | resistant |
| hsa-let-7g | 11 | 0.043 | 1.41 | resistant |
| [1]hsa-miR-23a* | 19 | 0.0106 | 1.54 | resistant |
| [2]hsa-miR-21 | 20 | 0.0621 | 1.75 | resistant |
| MID-00689 | 13 | 0.005 | 2.1 | sensitive |
| hsa-miR-378 | 15 | 0.0055 | 1.84 | sensitive |
| hsa-miR-625 | 17 | 0.029 | 1.81 | sensitive |

[1]hsa-miR-23a* did not pass the signal threshold of >300
[2]hsa-miR-21 did not pass the p-value cutoff (Mann-Whitney p Value < 0.05)

The differential expression of hsa-miR-27a (SEQ ID NO: 4), hsa-miR-378 (SEQ ID NO: 15) and hsa-miR-23a (SEQ ID NO: 6) between sensitive and resistant tumors was also observed in a subset of stage III patients (n=30) treated by the combined paclitaxel with carboplatin treatment, and in the subset of stage III serous tumors (n=25). With the exception of hsa-let-7g (SEQ ID NO: 11), which was over-expressed in serous papillary tumors (p=0.013), no difference was found between tumors of serous and endometrioid histologies with similar response to chemotherapy in the expression of relevant microRNAs.

Figure 2A:
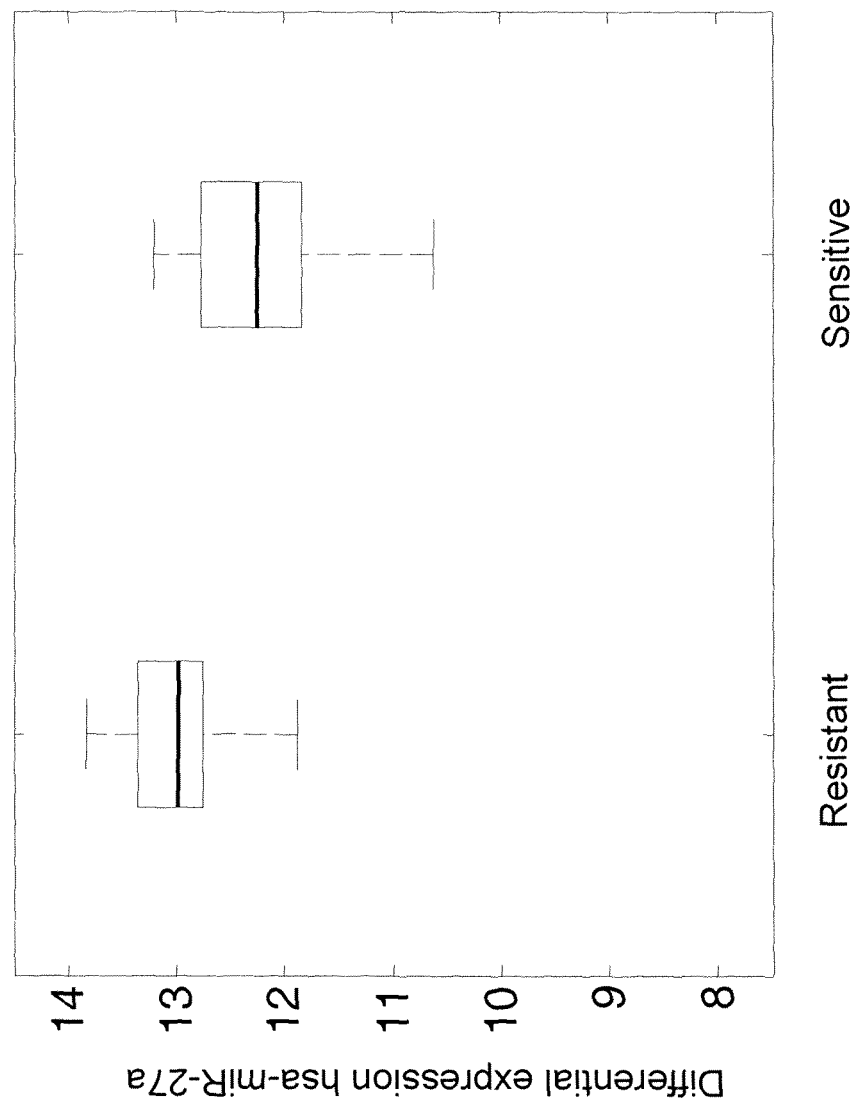
FIGS. 2a-2b show differential expression of microRNAs in stage III ovarian cancers that are resistant (left box) or sensitive (right box) to platinum-based treatment. Expression scale (y-axis) shows the logarithm (base 2) of the normalized fluorescence signal by microarray. Boxplots show the median (horizontal line), 25 to 75 percentile (box) and extent of data ("whiskers") for resistant (n=12) and sensitive (n=25) patients.
Figure 2B:
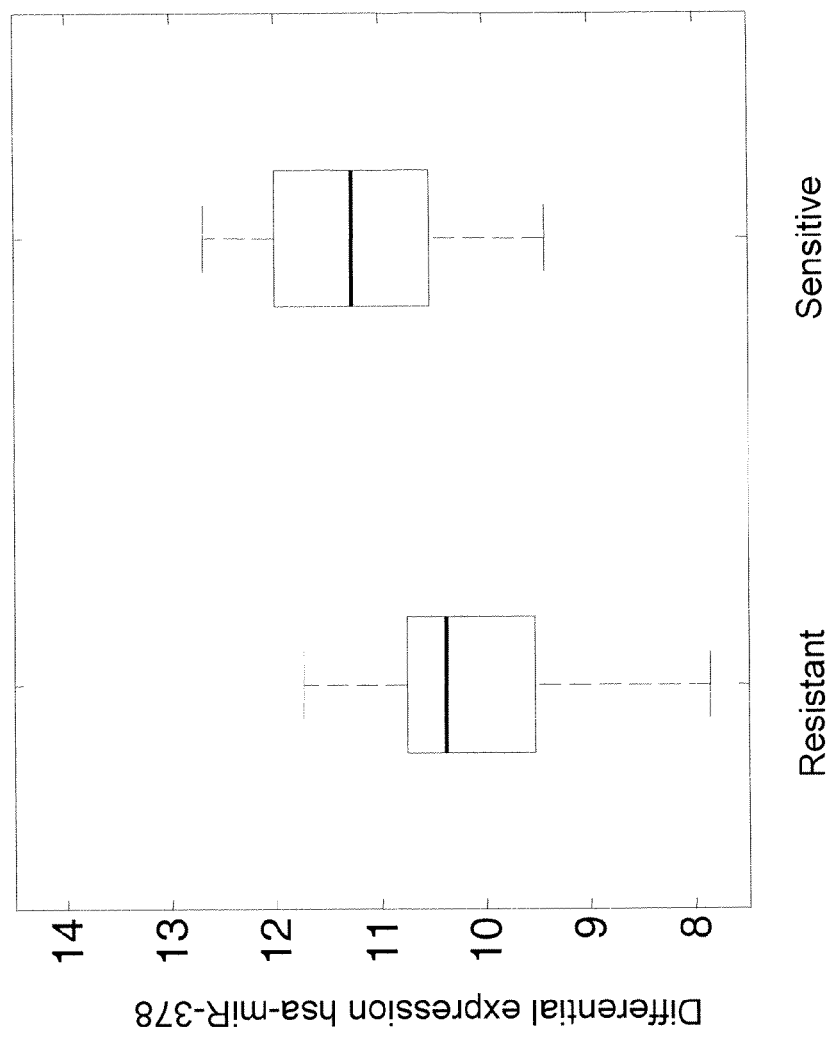
Figure 3A:
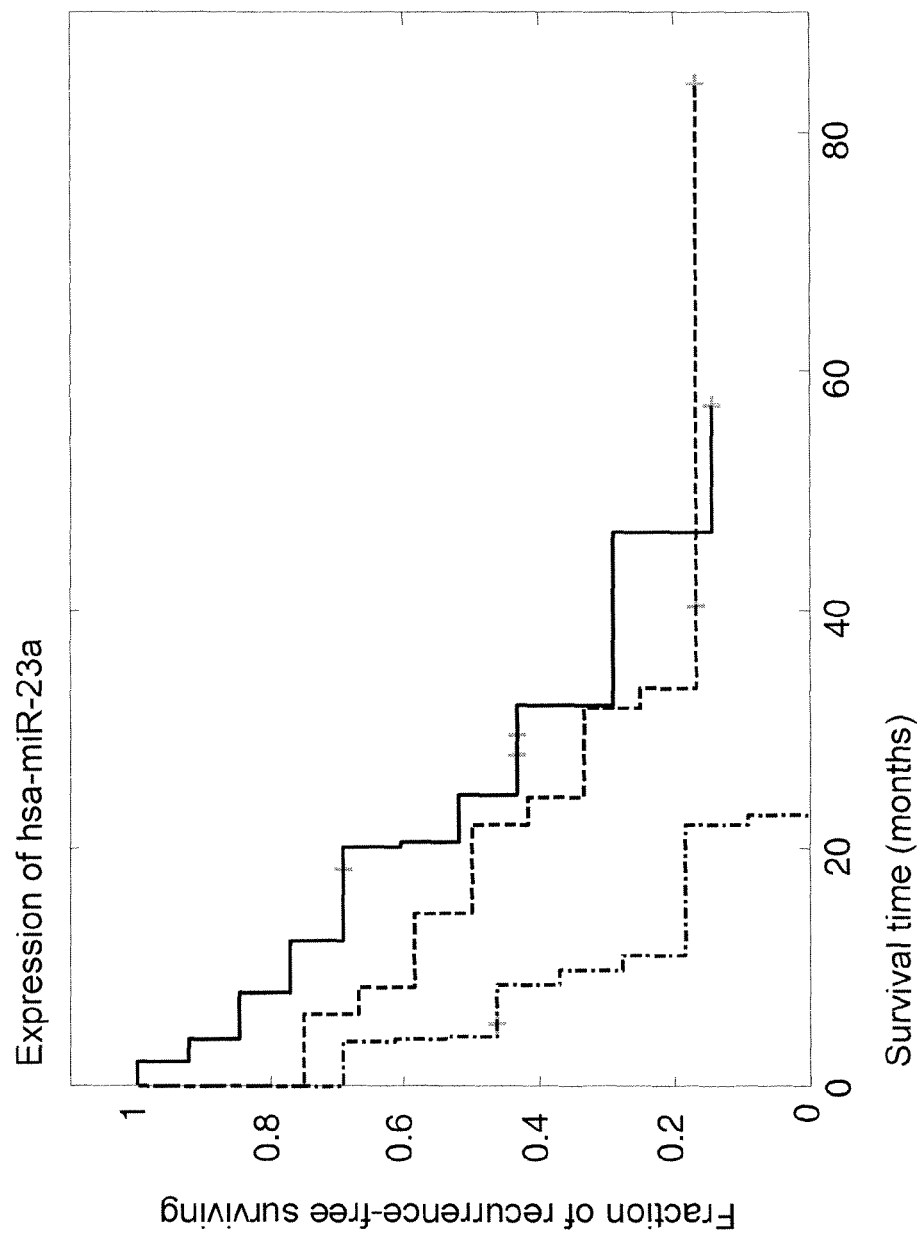
FIGS. 3a-3d show Kaplan Meier curves, which correct for patients who were censored (subjects that may have dropped out of the study and/or were lost to follow-up, or deliberately withdrawn). Censoring events are marked by gray vertical lines.
Figure 3B:
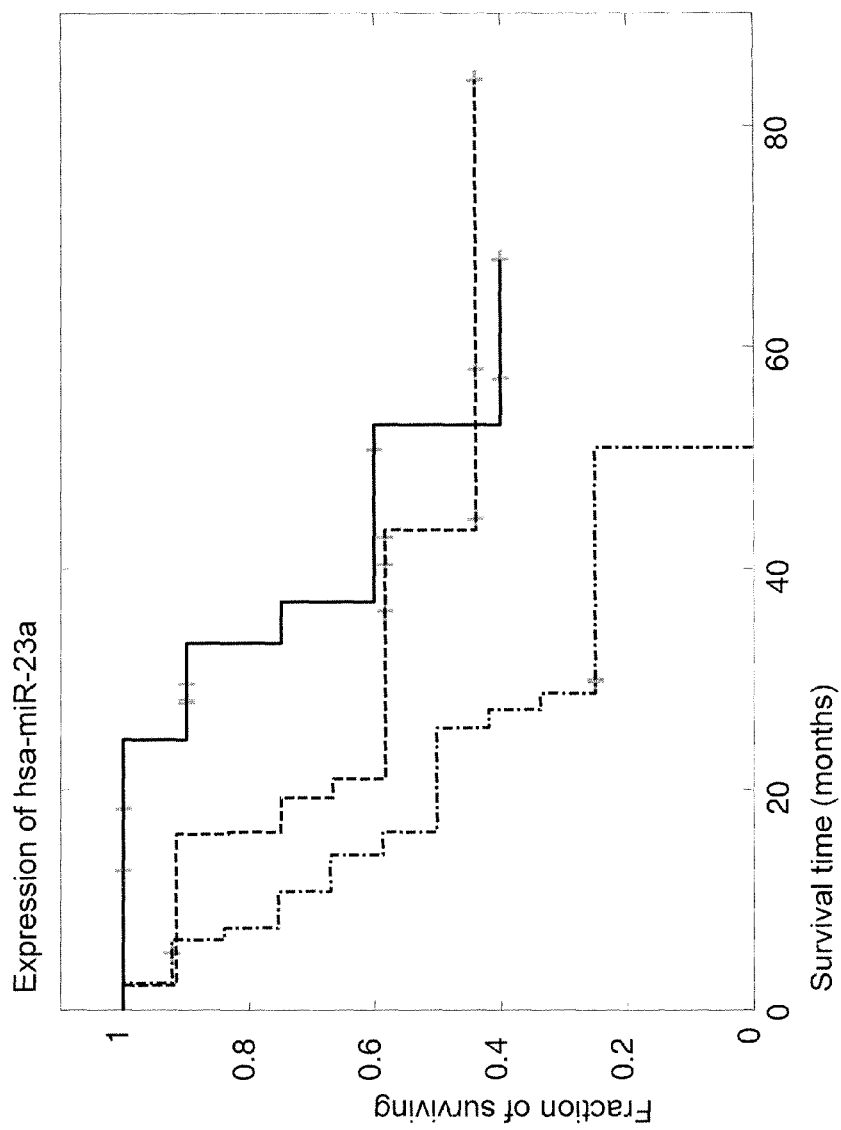
Figure 3C:
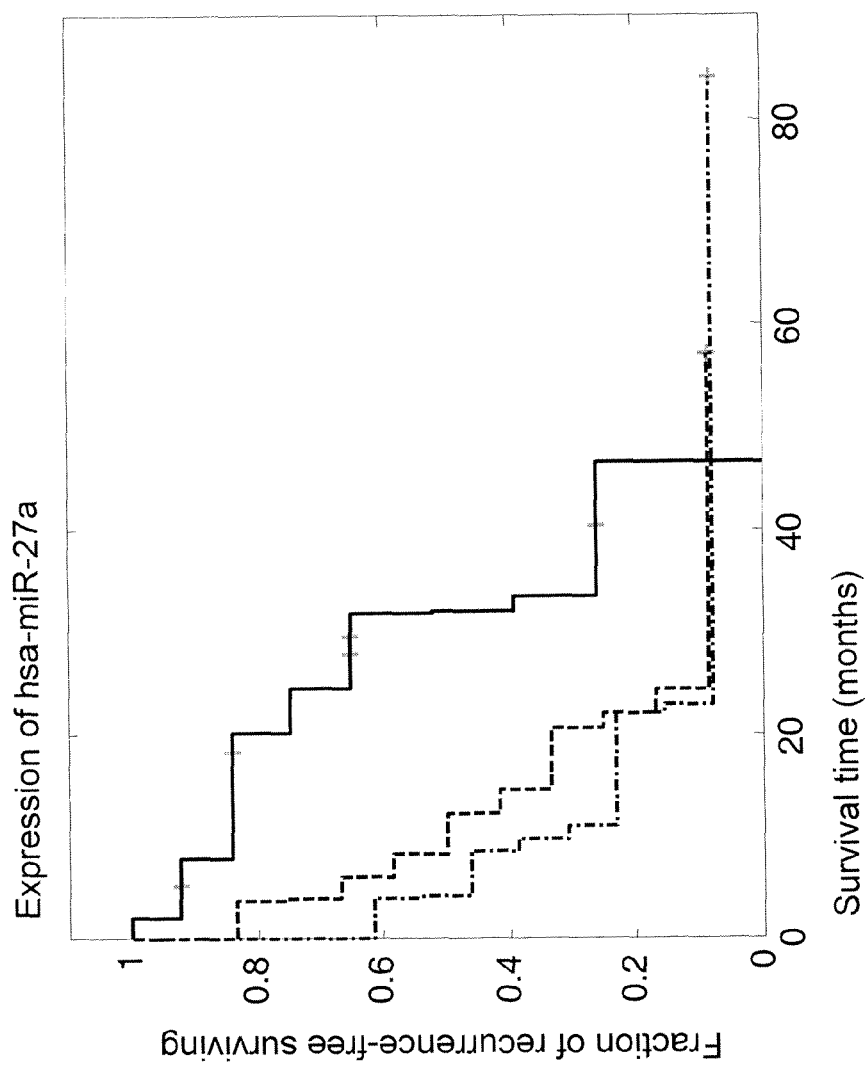
Figure 3D:
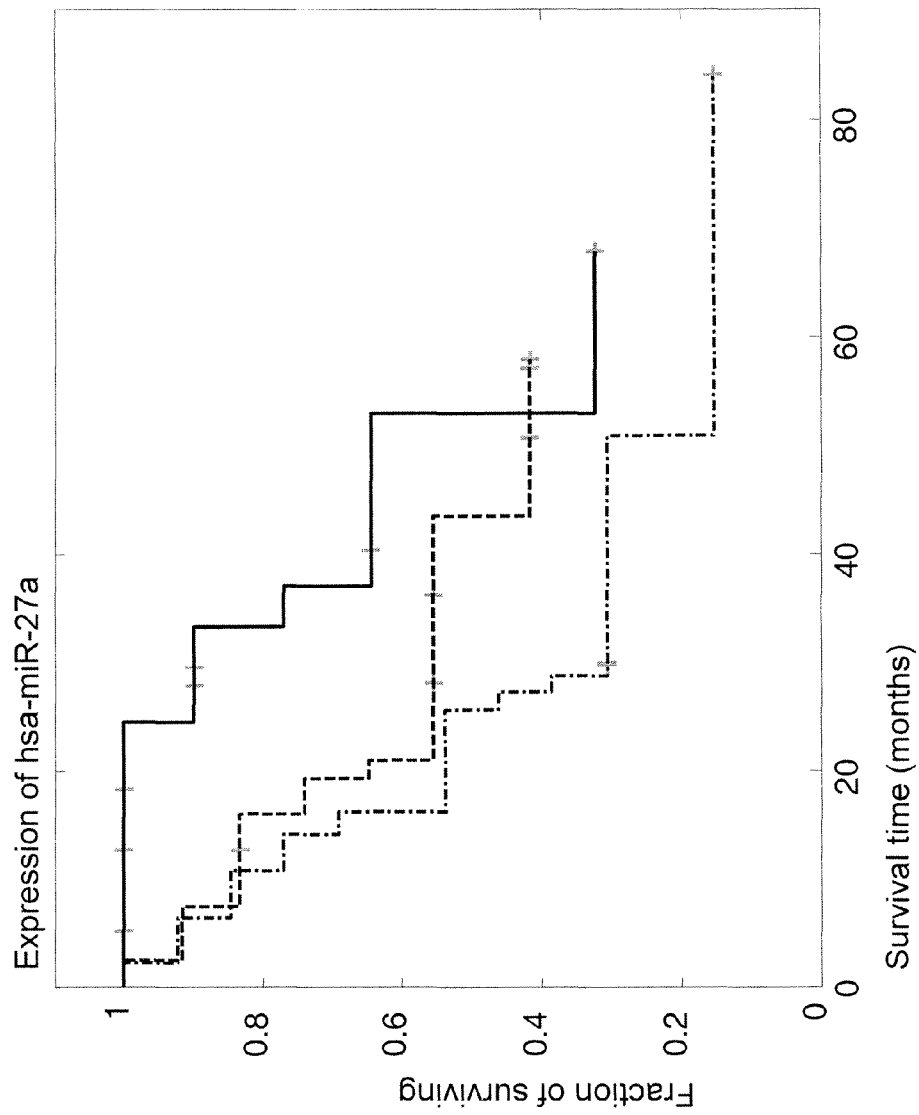

The distributions of two of the significantly differentially expressed miRs, hsa-miR-27a (SEQ ID NO: 4) and hsa-miR-378 (SEQ ID NO: 15), are presented in the boxplots of FIGS. 2a and 2b, respectively.

Accordingly, relatively high expressions of any of hsa-miR-199a-3p (SEQ ID NO: 1), hsa-miR-27a (SEQ ID NO: 4), hsa-miR-23a (SEQ ID NO: 6), hsa-miR-30c (SEQ ID NO: 8), hsa-let-7g (SEQ II) NO: 11), hsa-miR-23a* (SEQ ID NO: 19) and hsa-miR-21 (SEQ ID NO: 20) are predictive of platinum-resistance in tumors from patients with stage III ovarian cancer, and relatively high expression levels of any of MID-00689 (SEQ ID NO: 13), hsa-miR-378 (SEQ ID NO: 15) and hsa-miR-625 (SEQ ID NO: 17) are predictive of platinum-sensitivity in tumors from patients with stage III ovarian cancer.

Example 4: miR Expression Patterns in Patients with Stage III Ovarian Carcinoma Correlate with Prognosis The prognosis of groups of patients, stratified according the expression levels of individual microRNAs, was compared. For each microRNA the samples were divided into tertiles according to high (n=13), intermediate (n=12) or low (n=13) expression level of the microRNA.

Survival and time to progression were compared between the two groups with high and low microRNA expression levels. The microRNAs associated with significant differences (logrank p-value<0.05) in survival or time to progression are presented in Table 4.

TABLE 4

| | | p value | | |
|---|---|---|---|---|
| miR | SEQ ID NO. | time to progression | survival | higher expression associated with- |
| hsa-miR-27a | 4 | 0.0176 | 0.0215 | poorer prognosis |
| hsa-miR-23a | 6 | 0.0049 | 0.0025 | poorer prognosis |
| [1]hsa-miR-23a* | 19 | 0.0053 | 0.0007 | poorer prognosis |
| hsa-miR-21 | 20 | 0.0493 | 0.222 | poorer prognosis |

TABLE 4-continued

| miR | SEQ ID NO. | p value time to progression | p value survival | higher expression associated with- |
|---|---|---|---|---|
| hsa-miR-24-2* | 55 | 0.225 | 0.0493 | poorer prognosis |
| hsa-miR-449b | 22 | 0.1 | 0.0379 | better prognosis |

[1] hsa-miR-23a* did not pass the signal threshold of >300

The correlation between miR expression and survival time and time to progression in stage III patients is further indicated in FIGS. 3a-3d, which show Kaplan Meier plots of survival time and recurrence-free survival curves plotted for each of the three expression-level groups, for hsa-miR-23a (SEQ ID NO: 6) and hsa-miR-27a (SEQ ID NO: 4), which were associated with significant differences in both survival and recurrence-free survival.

Figure 5:
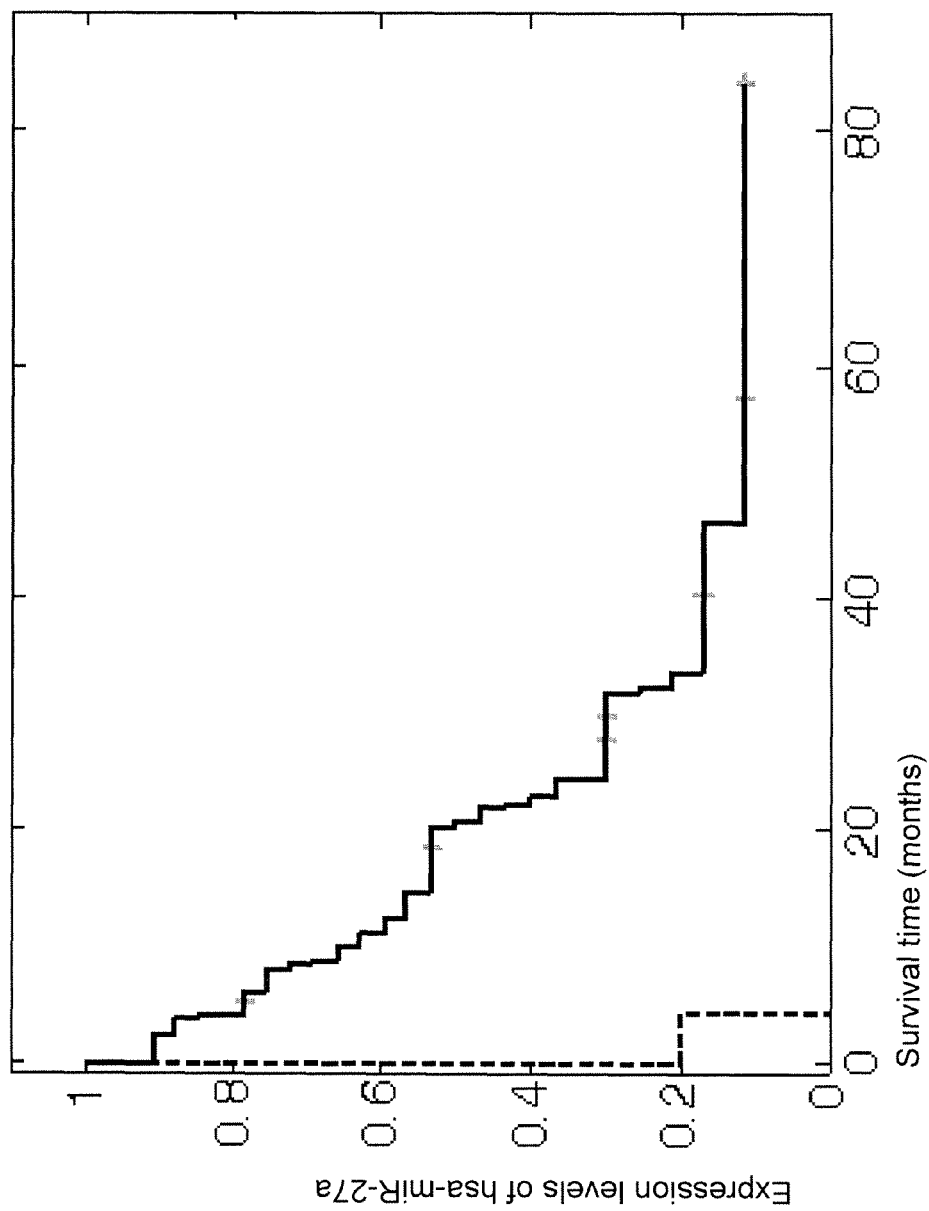
FIG. 5 shows Kaplan-Meier curves of recurrence-free survival for groups of patients of stage 3 disease, stratified by expression levels of hsa-miR-27a (SEQ ID NO: 4). Exceptionally high expression level of hsa-miR-27a identifies a subgroup of patients (n=5) with very poor prognosis. The samples with the highest expression level of hsa-miR-27a (normalized fluorescence signal>9500) had a very low time to progression and were resistant to platinum-based treatment, and most (4 out of 5) had an incomplete response. Samples with lower expression of hsa-miR-27a had a median survival time of 20.6 months.

Accordingly, in patients with stage III ovarian cancer, relatively high expressions of any of hsa-miR-27a (SEQ ID NO: 4), hsa-miR-23a (SEQ ID NO: 6), hsa-miR-23a* (SEQ ID NO: 19), hsa-miR-21 (SEQ ID NO: 20) and hsa-miR-24-2* (SEQ ID NO: 55) is predictive of a poor prognosis, whereas high expression of hsa-miR-449b (SEQ ID NO: 22) is indicative of better prognosis. Exceptionally high expression level of hsa-miR-27a (SEQ ID NO: 4) was further found to identify a subgroup of patients with very poor prognosis (FIG. 5) that had progressive disease during first line chemotherapy and extremely short progression-free survival.

In order to assess the relative contribution of various parameters on progression times in stage III, the Cox proportional hazards model was used. The parameters used were hsa-miR-27a (SEQ ID NO: 4) expression (b=0.99, p=0.02), grade (b=−0.15, p=0.76), age (b=0.03, p=0.13), optimal cytoreduction status (b=−1.1, p=0.05) and histological type (b=0.37, p=0.51). The results thus indicated that grade, age and histological type do not contribute to progression times within stage III beyond the effect of hsa-miR-27a expression and optimal debulking status. In order to further examine the connection between hsa-miR-27a expression and optimal cytoreduction status, the association of this microRNA with disease progression was analyzed separately for stage III patients with or without optimal cytoreduction. For patients with optimal cytoreduction, hsa-miR-27a was not a good predictor of progression times (logrank p-value of 0.62, comparing the upper and lower tertiles). However, interestingly, for patients without optimal debulking, hsa-miR-27a was a significant predictor of progression times (logrank p-value of 0.046, comparing the upper and lower tertiles).

Figure 4B:
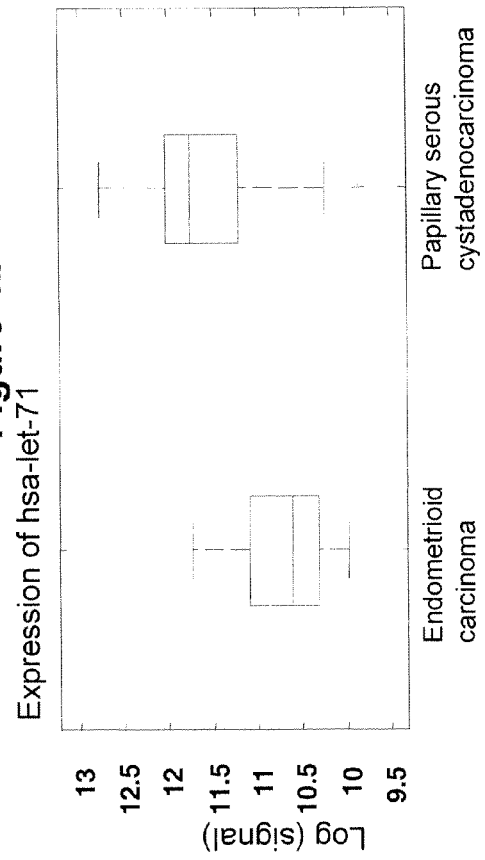
FIGS. 4a-4b show boxplot presentations of microRNAs comparing the distributions between the expressions of hsa-miR-93 (SEQ ID NO: 34, FIG. 4a) and hsa-miR-let-7i (SEQ ID NO: 32, FIG. 4b) in stage III of ovarian cancer patients with endometrioid carcinoma tumors (n=13) and papillary serous cystadenocarcinoma tumors (n=25) histological subtypes. The "box" part contains 50% of the data, the line in the box indicates the median value, and the ends of the vertical lines indicate the minimum and maximum data values. The Y-axis represents the log(signal).
Figure 4A:
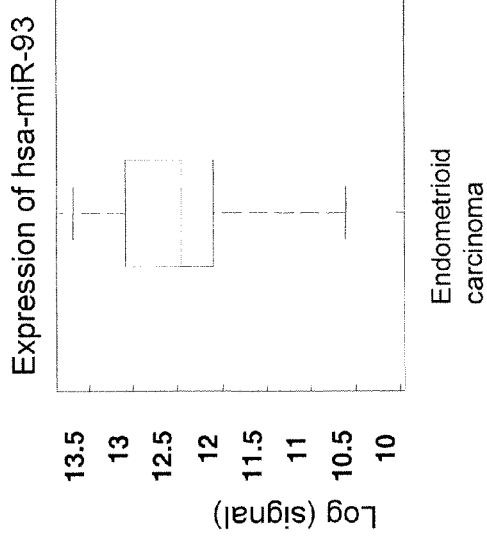

Example 5: miR Expression Patterns in Patients with Stage III Ovarian Carcinoma Correlate with Histological Subtype The miR expression patterns of stage III ovarian cancer were examined in tumors of various histological subtypes. As indicated in FIG. 4, the expression of hsa-miR-93 (SEQ ID NO: 34) in endometrioid carcinoma tumors (n=13) was two fold higher than its expression in papillary serous cystadenocarcinoma tumors (n=25), with a p-value of 0.004216. Contrastingly, the expression of hsa-let-7i (SEQ ID NO. 32) in cystadenocarcinoma tumors was 2.2-fold higher than in endometrioid carcinoma tumors, with a p-value of 0.000637. These two miRs were significant when limiting the False Detection Rate (FDR) to 0.1. Several other miRs were significant using this threshold, although with a lower fold change. These include hsa-let-7g (SEQ ID NO: 11) (P=0.0005, 1.6 fold higher in serous cystadenocarcinoma). Accordingly, the expression pattern of endometrioid carcinoma tumors differs significantly from the expression pattern of cystadenocarcinoma tumors.

Example 6: Therapeutic Uses of hsa-miR-449A (SEQ ID NO: 24), hsa-miR-449B (SEQ ID NO: 22) and hsa-miR-200A (SEQ ID NO: 30)

Hsa-miR-449b (SEQ ID NO: 22) and hsa-miR-449a (SEQ ID NO: 24) bear a high similarity in sequence to the hsa-miR-34 family. In particular, residues 2-8 (5' end) of hsa-miR-449 are identical to those of hsa-miR-34a (SEQ ID NO: 36). Residues 2-8 of microRNAs, also referred to as the "seed" sequence, are the most strongly conserved sequences in microRNAs and microRNA families and are considered the most important for determination of mRNA targets of microRNAs. Thus, similarity in the seed sequence may suggest similar activity in a cancer cell.

The common seed of hsa-miR-449a (SEQ ID NO: 24) and hsa-miR-44911 (SEQ ID NO: 22) is identical to the seeds of most of the members of the hsa-miR-34 family. The sequences of the hsa-miR-34 and the hsa-miR-449 families are presented in table 5, with the sequences of the seeds underlined.

TABLE 5

| hsa-miR-34a | SEQ ID NO: 36 | T GGCAGTGTC TT AGCTGGTTGT |
| hsa-miR-34b* | SEQ ID NO: 37 | TAGGCAGTGTCATT AGCTGATTG |
| hsa-miR-34c-5p | SEQ ID NO: 28 | AGGCAGTGTAGTT AGCTGATTGC |
| hsa-miR-449a | SEQ ID NO: 24 | TGGCAGTGT ATTG TTAGCTGGT |
| hsa-miR-449b | SEQ ID NO: 22 | AGGCAGTGT ATTG TTAGCTGGC |

According to the present invention, hsa-miR-34a (SEQ ID NO: 36) was down-regulated in advanced (stage III) tumors. Hsa-miR-449b (SEQ 11) NO: 22) was similarly down-regulated in advanced tumors while its high expression was associated with a better response to platinum-based chemotherapy among stage III cases.

He et al. (Nature 2007; 447:1130-4) have shown that genes encoding miRNAs in the miR-34 family are direct transcriptional targets of p53, and that ectopic expression of miR-34 induces cell cycle arrest in both primary and tumor-derived cell lines. p53 is an important tumor suppressor gene in many human cancers including ovarian carcinoma. Mutations in p53 are known to be associated with tumor aggressiveness and prognosis. miRNA components of tumor suppressor pathways have been described by comparing miRNA expression profiles of wild-type and p53-deficient cells.

In addition to regulating the expression of hundreds of protein-coding genes, p53 also modulates the levels of miRNAs. p53 can induce expression of miR-34a (SEQ ID NO: 36) in cultured cells as well as in irradiated mice, by binding to a perfect p53 binding site located within the gene that gives rise to miR-34a (SEQ ID NO: 36). Inactivation of miR-34a (SEQ ID NO: 36) strongly attenuates p53-mediated apoptosis in cells exposed to genotoxic stress, whereas overexpression of miR-34a (SEQ ID NO: 36) mildly increases apoptosis. Hence, miR-34a (SEQ ID NO: 36) is a direct pro-apoptotic transcriptional target of p53 that can mediate some of p53's biological effects. It has been postulated that decreased expression of miR-34a (SEQ ID NO: 36) may contribute to tumorigenesis by attenuating p53-dependent apoptosis (Nina Raver-Shapira, et. al, Mol Cell, 2007; 26:731-743).

The similarity between the seed sequence of the hsa-miR-34 and the hsa-miR-449 families may suggest similar activity. The level of hsa-miR-449b (SEQ ID NO: 22) was also found to differ significantly between stages (4.6-fold higher in stage I vs. stage III, P=0.048). Taken together with its correlation to stage, and to better prognosis as described in Example 4, this makes hsa-miR-449b (SEQ ID NO: 22) a promising therapeutic target.

A significant difference between stage I and stage III was also found for hsa-miR-200a (SEQ ID NO: 30) (p=0.00047, 2.1 fold higher in Stage I). Yang and coworkers recently studied expression of microRNA in ovarian cancers of different stages (Yang H. et al. Cancer Res. 2008 68: 425-433). Using a set of ovarian tumors of mixed histologies, they found high expression of hsa-miR-200a (SEQ ID NO: 30) associated with higher stage ovarian cancers. Nam and coworkers recently described a correlation between tumor expression of microRNAs and cumulative survival in ovarian carcinoma tumor samples (Nam E J. Clin Cancer Res 2008; 14(9):2690-5). In their data, high expression of hsa-miR-200a (SEQ ID NO: 30) was associated with tumors from patients with poorer survival. In contrast to their findings, in the data set of the present invention, significantly higher expression of hsa-miR-200a (SEQ ID NO: 30) was found in early stage disease, correlating with improved survival. In the study by Nam and coworkers, no data is provided regarding stage at diagnosis and its correlation to miR expression. The study by Yang and coworkers included significant numbers of mucinous and clear cell cystadenocarcinomas, histologies not represented in the present study. This might explain the discrepancy between the studies. Accordingly, hsa-miR-200a (SEQ ID NO: 30) is also an interesting candidate for therapeutics.

Example 7: Genes Targeted by miRs Upregulated in Poor Prognosis

MicroRNA targets were selected from the intersection of the target prediction results by Targetscan and Miranda. Only targets with a Targetscan score lower than −0.2 were used. In order to retrieve only the most relevant targets, only genes targeted by at least two microRNAs were analyzed. The selected target genes include EIF4EBP2, which is a target of hsa-miR-21 (SEQ ID NO: 20), hsa-miR-23a (SEQ ID NO: 6) and less significantly of hsa-let-7g (SEQ ID NO: 11), and EIF4E3, a target of hsa-miR-23a (SEQ ID NO: 6) and less significantly hsa-miR-27a (SEQ ID NO: 4). These genes, together with EIF4G2 (a predicted target of hsa-let-7g, SEQ ID NO: 11), take part in the eIF4F complex (Sonenberg N. Biochem Cell Biol. 2008; 86(2):178-83) which was found to be associated with good prognosis in ovarian cancer (Armengol G, et al. Cancer Res. 2007; 67(16):7551-5). Thus, high levels of hsa-miR-21 (SEQ ID NO: 20), hsa-miR-23a (SEQ ID NO: 6), hsa-miR27a (SEQ ID NO: 4) and hsa-let-7g (SEQ ID NO: 11) may contribute to poor prognosis or chemotherapy resistance through their effect on this complex.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It should be understood that the detailed description and specific examples, while indicating preferred embodiments of the invention, are given by way of illustration only, since various changes and modifications within the spirit and scope of the invention will become apparent to those skilled in the art from this detailed description.

The invention claimed is:

1. A method of predicting poor prognosis for progression of platinum-resistant stage III ovarian cancer in response to platinum-based chemotherapy in a human subject comprising:
   (a) providing nucleic acids from an ovarian tumor sample obtained from a subject;
   (b) determining an expression level of SEQ ID NO: 6 in said ovarian tumor sample nucleic acids by a real-time polymerase chain reaction method comprising hybridizing said nucleic acids with a probe, wherein the sequence of the probe consists of a full complement of SEQ ID NO: 6 and a linker of 10-60 nucleotides attached to the 3' end of the complement of SEQ ID NO: 6; and
   (c) comparing said expression level to a threshold expression level, and determining if the expression level of SEQ ID NO: 6 in said ovarian tumor sample nucleic acids is above said threshold expression level; and
   (d) predicting progression of platinum-resistant stage III ovarian cancer in response to platinum-based chemotherapy in said subject based on increased expression of SEQ ID NO: 6 in said ovarian tumor sample nucleic acids relative to said threshold expression level,
   wherein increased expression of SEQ ID NO: 6 is predictive of poor prognosis for progression of platinum-resistant stage III ovarian cancer, and wherein said threshold expression level is the expression level of SEQ ID NO: 6 in a platinum-sensitive ovarian cancer.

2. The method of claim 1, wherein the platinum-based agent is selected from the group consisting of carboplatin and cisplatin.

3. The method of claim 1, wherein said ovarian tumor sample is a tumor tissue of a specific histological subtype.

4. The method of claim 3, wherein said histological subtype is selected from the group consisting of papillary serous cystadenocarcinoma and endometrioid carcinoma.

5. The method of claim 1, wherein said ovarian tumor sample is a tissue sample.

6. The method of claim 5, wherein said tissue is a fresh, frozen, fixed, wax-embedded or formalin fixed paraffin-embedded (FFPE) tissue.

7. The method of claim 1, wherein the real-time PCR method comprises forward and reverse primers.

* * * * *

SEQUENCE LISTING

```
<160> NUMBER OF SEQ ID NOS: 71

<210> SEQ ID NO 1
<211> LENGTH: 22
<212> TYPE: RNA
<213> ORGANISM: Homo sapiens

<400> SEQUENCE: 1
acaguagucu gcacauuggu ua                                              22

<210> SEQ ID NO 2
<211> LENGTH: 71
<212> TYPE: RNA
<213> ORGANISM: Homo sapiens

<400> SEQUENCE: 2
gccaacccag uguucagacu accuguucag gaggcucuca auguguacag uagucugcac    60
auugguuagg c                                                          71
```

```
<210> SEQ ID NO 3
<211> LENGTH: 110
<212> TYPE: RNA
<213> ORGANISM: Homo sapiens

<400> SEQUENCE: 3
aggaagcuuc uggagauccu gcuccgucgc cccaguguuc agacuaccug uucaggacaa    60
ugccguugua caguagucug cacauugguu agacugggca agggagagca              110

<210> SEQ ID NO 4
<211> LENGTH: 21
<212> TYPE: RNA
<213> ORGANISM: Homo sapiens

<400> SEQUENCE: 4
uucacagugg cuaaguuccg c                                             21

<210> SEQ ID NO 5
<211> LENGTH: 78
<212> TYPE: RNA
<213> ORGANISM: Homo sapiens

<400> SEQUENCE: 5
cugaggagca gggcuuagcu gcuugugagc agguccaca ccaagucgug uucacagugg    60
cuaaguuccg cccccccag                                                78

<210> SEQ ID NO 6
<211> LENGTH: 21
<212> TYPE: RNA
<213> ORGANISM: Homo sapiens

<400> SEQUENCE: 6
aucacauugc cagggauuuc c                                             21

<210> SEQ ID NO 7
<211> LENGTH: 73
<212> TYPE: RNA
<213> ORGANISM: Homo sapiens

<400> SEQUENCE: 7
ggccggcugg gguuccuggg gaugggauuu gcuuccuguc acaaaucaca uugccaggga    60
uuuccaaccg acc                                                      73

<210> SEQ ID NO 8
<211> LENGTH: 23
<212> TYPE: RNA
<213> ORGANISM: Homo sapiens

<400> SEQUENCE: 8
uguaaacauc cuacacucuc agc                                           23

<210> SEQ ID NO 9
<211> LENGTH: 89
<212> TYPE: RNA
<213> ORGANISM: Homo sapiens

<400> SEQUENCE: 9
accaugcugu agugugugua aacauccuac acucucagcu gugagcucaa gguggcuggg    60 agagggguugu uuacuccuuc ugccaugga                                    89
```

```
<210> SEQ ID NO 10
<211> LENGTH: 72
<212> TYPE: RNA
<213> ORGANISM: Homo sapiens

<400> SEQUENCE: 10
agauacugua aacauccuac acucucagcu guggaaagua agaaagcugg gagaaggcug      60
uuuacucuuu cu                                                         72

<210> SEQ ID NO 11
<211> LENGTH: 22
<212> TYPE: RNA
<213> ORGANISM: Homo sapiens

<400> SEQUENCE: 11
ugagguagua guuguacag uu                                               22

<210> SEQ ID NO 12
<211> LENGTH: 84
<212> TYPE: RNA
<213> ORGANISM: Homo sapiens

<400> SEQUENCE: 12
aggcugaggu aguaguuugu acaguuugag ggucuaugau accacccggu acaggagaua     60
acuguacagg ccacugccuu gcca                                            84

<210> SEQ ID NO 13
<211> LENGTH: 22
<212> TYPE: RNA
<213> ORGANISM: Homo sapiens

<400> SEQUENCE: 13
uggacuugga gucaggaggc cu                                              22

<210> SEQ ID NO 14
<211> LENGTH: 78
<212> TYPE: RNA
<213> ORGANISM: Homo sapiens

<400> SEQUENCE: 14
gagucacagu ggacuuggag ucaggaggcc ugagguccuu gaagaccucc cugaccugcu     60
cugguccacu gugugcuc                                                   78

<210> SEQ ID NO 15
<211> LENGTH: 21
<212> TYPE: RNA
<213> ORGANISM: Homo sapiens

<400> SEQUENCE: 15
acuggacuug gagucagaag g                                               21

<210> SEQ ID NO 16
<211> LENGTH: 66
<212> TYPE: RNA
<213> ORGANISM: Homo sapiens

<400> SEQUENCE: 16
agggcuccug acuccagguc cuguguguua ccuagaaaua gcacuggacu uggagucaga     60
aggccu                                                                66

<210> SEQ ID NO 17
```

```
<211> LENGTH: 21
<212> TYPE: RNA
<213> ORGANISM: Homo sapiens

<400> SEQUENCE: 17 aggggggaaag uucuauaguc c                                              21

<210> SEQ ID NO 18
<211> LENGTH: 85
<212> TYPE: RNA
<213> ORGANISM: Homo sapiens

<400> SEQUENCE: 18
aggguagagg gaugagggggg aaaguucuau aguccuguaa uuagaucuca ggacuauaga     60
acuuuccccc ucaucccucu gcccu                                           85

<210> SEQ ID NO 19
<211> LENGTH: 22
<212> TYPE: RNA
<213> ORGANISM: Homo sapiens

<400> SEQUENCE: 19 ggggguuccug gggaugggau uu                                             22

<210> SEQ ID NO 20
<211> LENGTH: 22
<212> TYPE: RNA
<213> ORGANISM: Homo sapiens

<400> SEQUENCE: 20
uagcuuauca gacugauguu ga                                              22

<210> SEQ ID NO 21
<211> LENGTH: 72
<212> TYPE: RNA
<213> ORGANISM: Homo sapiens

<400> SEQUENCE: 21
ugucggguag cuuaucagac ugauguugac uguugaaucu cauggcaaca ccagucgaug     60
ggcugucuga ca                                                         72

<210> SEQ ID NO 22
<211> LENGTH: 22
<212> TYPE: RNA
<213> ORGANISM: Homo sapiens

<400> SEQUENCE: 22
aggcagugua uuguuagcug gc                                              22

<210> SEQ ID NO 23
<211> LENGTH: 97
<212> TYPE: RNA
<213> ORGANISM: Homo sapiens

<400> SEQUENCE: 23
ugaccugaau cagguaggca guguauuguu agcuggcugc uugggucaag ucagcagcca     60
caacuacccu gccacuugcu ucuggauaaa uucuucu                              97

<210> SEQ ID NO 24
<211> LENGTH: 22
<212> TYPE: RNA
```

```
<400> SEQUENCE: 24
uggcagugua uuguuagcug gu                                               22

<210> SEQ ID NO 25
<211> LENGTH: 91
<212> TYPE: RNA
<213> ORGANISM: Homo sapiens

<400> SEQUENCE: 25
cuguguguga ugagcuggca guguauuguu agcugguuga auaugugaau ggcaucggcu      60
aacaugcaac ugcugucuua uugcauauac a                                    91

<210> SEQ ID NO 26
<211> LENGTH: 22
<212> TYPE: RNA
<213> ORGANISM: Homo sapiens

<400> SEQUENCE: 26
uuaucagaau cuccagggu ac                                                22

<210> SEQ ID NO 27
<211> LENGTH: 72
<212> TYPE: RNA
<213> ORGANISM: Homo sapiens

<400> SEQUENCE: 27
ggagcuuauc agaaucucca gggguacuuu auaauuucaa aaagucccccc aggugugauu     60 cugauuugcu uc                                                         72

<210> SEQ ID NO 28
<211> LENGTH: 23
<212> TYPE: RNA
<213> ORGANISM: Homo sapiens

<400> SEQUENCE: 28
aggcagugua guuagcugau ugc                                             23

<210> SEQ ID NO 29
<211> LENGTH: 77
<212> TYPE: RNA
<213> ORGANISM: Homo sapiens

<400> SEQUENCE: 29
agucuaguua cuaggcagug uaguuagcug auugcuaaua guaccaauca cuaaccacac      60
ggccagguaa aaagauu                                                    77

<210> SEQ ID NO 30
<211> LENGTH: 22
<212> TYPE: RNA
<213> ORGANISM: Homo sapiens

<400> SEQUENCE: 30
uaacacuguc ugguaacgau gu                                              22

<210> SEQ ID NO 31
<211> LENGTH: 90
<212> TYPE: RNA
<213> ORGANISM: Homo sapiens

<400> SEQUENCE: 31
```

```
ccgggccccu gugagcaucu uaccggacag ugcuggauuu cccagcuuga cucuaacacu    60
gucugguaac gauguucaaa ggugacccgc                                     90
```

<210> SEQ ID NO 32
<211> LENGTH: 22
<212> TYPE: RNA
<213> ORGANISM: Homo sapiens

<400> SEQUENCE: 32

```
ugagguagua guuugugcug uu                                             22
```

<210> SEQ ID NO 33
<211> LENGTH: 84
<212> TYPE: RNA
<213> ORGANISM: Homo sapiens

<400> SEQUENCE: 33

```
cuggcugagg uaguaguuug ugcuguuggu cgguuguga cauugcccgc uguggagaua     60
acugcgcaag cuacugccuu gcua                                           84
```

<210> SEQ ID NO 34
<211> LENGTH: 23
<212> TYPE: RNA
<213> ORGANISM: Homo sapiens

<400> SEQUENCE: 34

```
caaagugcug uucgugcagg uag                                            23
```

<210> SEQ ID NO 35
<211> LENGTH: 80
<212> TYPE: RNA
<213> ORGANISM: Homo sapiens

<400> SEQUENCE: 35

```
cuggggcuc caaagugcug uucgugcagg uagugugauu acccaaccua cugcugagcu     60
agcacuuccc gagcccccgg                                                80
```

<210> SEQ ID NO 36
<211> LENGTH: 22
<212> TYPE: RNA
<213> ORGANISM: Homo sapiens

<400> SEQUENCE: 36

```
uggcaguguc uuagcugguu gu                                             22
```

<210> SEQ ID NO 37
<211> LENGTH: 23
<212> TYPE: RNA
<213> ORGANISM: Homo sapiens

<400> SEQUENCE: 37

```
uaggcagugu cauuagcuga uug                                            23
```

<210> SEQ ID NO 38
<211> LENGTH: 110
<212> TYPE: RNA
<213> ORGANISM: Homo Sapiens

<400> SEQUENCE: 38

```
ggccagcugu gaguguuucu uuggcagugu cuuagcuggu uguugagc aauaguaagg      60 aagcaaucag caaguauacu gcccuagaag ugcugcacgu ugugggccc                110
```

```
<210> SEQ ID NO 39
<211> LENGTH: 84
<212> TYPE: RNA
<213> ORGANISM: Homo Sapiens

<400> SEQUENCE: 39
gugcucgguu uguaggcagu gucauuagcu gauuguacug uggugguuac aaucacuaac    60
uccacugcca ucaaaacaag gcac                                          84

<210> SEQ ID NO 40
<211> LENGTH: 22
<212> TYPE: RNA
<213> ORGANISM: Homo Sapiens

<400> SEQUENCE: 40
uaauacugcc ugguaaugau ga                                            22

<210> SEQ ID NO 41
<211> LENGTH: 18
<212> TYPE: RNA
<213> ORGANISM: Homo Sapiens

<400> SEQUENCE: 41
uucacaggga ggugucau                                                 18

<210> SEQ ID NO 42
<211> LENGTH: 22
<212> TYPE: RNA
<213> ORGANISM: Homo Sapiens

<400> SEQUENCE: 42
ugauugguac gucugugggu ag                                            22

<210> SEQ ID NO 43
<211> LENGTH: 22
<212> TYPE: RNA
<213> ORGANISM: Homo Sapiens

<400> SEQUENCE: 43
uacugcagac guggcaauca ug                                            22

<210> SEQ ID NO 44
<211> LENGTH: 23
<212> TYPE: RNA
<213> ORGANISM: Homo Sapiens

<400> SEQUENCE: 44
ugagugugug ugugugagug ugu                                           23

<210> SEQ ID NO 45
<211> LENGTH: 23
<212> TYPE: RNA
<213> ORGANISM: Homo Sapiens

<400> SEQUENCE: 45
agcucggucu gaggccccuc agu                                           23

<210> SEQ ID NO 46
<211> LENGTH: 22
<212> TYPE: RNA
<213> ORGANISM: Homo Sapiens
```

```
<400> SEQUENCE: 46
cagugcaaug uuaaaagggc au                                          22

<210> SEQ ID NO 47
<211> LENGTH: 22
<212> TYPE: RNA
<213> ORGANISM: Homo Sapiens

<400> SEQUENCE: 47
ugagaacuga auuccauagg cu                                          22

<210> SEQ ID NO 48
<211> LENGTH: 22
<212> TYPE: RNA
<213> ORGANISM: Homo Sapiens

<400> SEQUENCE: 48
aacuggccua caaaguccca gu                                          22

<210> SEQ ID NO 49
<211> LENGTH: 22
<212> TYPE: RNA
<213> ORGANISM: Homo Sapiens

<400> SEQUENCE: 49
ugggucuuug cgggcgagau ga                                          22

<210> SEQ ID NO 50
<211> LENGTH: 22
<212> TYPE: RNA
<213> ORGANISM: Homo Sapiens

<400> SEQUENCE: 50 agugggaac ccuuccauga gg                                           22

<210> SEQ ID NO 51
<211> LENGTH: 21
<212> TYPE: RNA
<213> ORGANISM: Homo Sapiens

<400> SEQUENCE: 51
aucacauugc cagggauuac c                                           21

<210> SEQ ID NO 52
<211> LENGTH: 22
<212> TYPE: RNA
<213> ORGANISM: Homo Sapiens

<400> SEQUENCE: 52
acaggugagg uucuugggag cc                                          22

<210> SEQ ID NO 53
<211> LENGTH: 24
<212> TYPE: RNA
<213> ORGANISM: Homo Sapiens

<400> SEQUENCE: 53
ucccugagac ccuuuaaccu guga                                        24

<210> SEQ ID NO 54
<211> LENGTH: 22
<212> TYPE: RNA
<213> ORGANISM: Homo Sapiens
```

```
<400> SEQUENCE: 54
aaaccguuac cauuacugag uu                                          22

<210> SEQ ID NO 55
<211> LENGTH: 22
<212> TYPE: RNA
<213> ORGANISM: Homo Sapiens

<400> SEQUENCE: 55
ugccuacuga gcugaaacac ag                                          22

<210> SEQ ID NO 56
<211> LENGTH: 95
<212> TYPE: RNA
<213> ORGANISM: Homo Sapiens

<400> SEQUENCE: 56
ccagcucggg cagccguggc caucuuacug ggcagcauug gauggaguca ggucucuaau  60
acugccuggu aaugaugacg gcggagcccu gcacg                            95

<210> SEQ ID NO 57
<211> LENGTH: 127
<212> TYPE: RNA
<213> ORGANISM: Homo Sapiens

<400> SEQUENCE: 57
ggaugccaca uucagccauu cagugugcag ugccuuucac agggaggugu cauuuaugug  60
aacuaaaaua uaaauuucac cuuucugaga aggguaaugu acagcaugca cugcauaugu 120
ggugucc                                                          127

<210> SEQ ID NO 58
<211> LENGTH: 94
<212> TYPE: RNA
<213> ORGANISM: Homo Sapiens

<400> SEQUENCE: 58
caugcugugu gugguacccu acugcagaca guggcaauca uguauaauua aaaugauug   60 guacgucugu ggguagagua cugcaugaca caug                             94

<210> SEQ ID NO 59
<211> LENGTH: 75
<212> TYPE: RNA
<213> ORGANISM: Homo Sapiens

<400> SEQUENCE: 59
gugguacccu acugcagacg uggcaaucau guauaauuaa aaaugauugg uacgucugug  60
gguagaguac ugcau                                                  75

<210> SEQ ID NO 60
<211> LENGTH: 96
<212> TYPE: RNA
<213> ORGANISM: Homo Sapiens

<400> SEQUENCE: 60
gggaccugcg uggguggcggg cgugugagug ugugugugug agugugguc gcuccggguc  60 cacgcucaug cacacaccca cacgcccaca cucagg                           96

<210> SEQ ID NO 61
```

```
<211> LENGTH: 94
<212> TYPE: RNA
<213> ORGANISM: Homo Sapiens

<400> SEQUENCE: 61
auaaaggaag uuaggcugag gggcagagag cgagacuuuu cuauuuucca aaagcucggu     60
cugaggcccc ucagucuugc uuccuaaccc gcgc                                94

<210> SEQ ID NO 62
<211> LENGTH: 89
<212> TYPE: RNA
<213> ORGANISM: Homo Sapiens

<400> SEQUENCE: 62
ugcugcuggc cagagcucuu uucacauugu gcuacugucu gcaccuguca cuagcagugc     60
aauguuaaaa gggcauuggc cguguagug                                      89

<210> SEQ ID NO 63
<211> LENGTH: 73
<212> TYPE: RNA
<213> ORGANISM: Homo Sapiens

<400> SEQUENCE: 63
ccuggcacug agaacugaau uccauaggcu gugagcucua gcaaugcccu guggacucag     60
uucuggugcc cgg                                                       73

<210> SEQ ID NO 64
<211> LENGTH: 88
<212> TYPE: RNA
<213> ORGANISM: Homo Sapiens

<400> SEQUENCE: 64
cgaggauggg agcugagggc ugggucuuug cgggcgagau gagggugucg gaucaacugg     60
ccuacaaagu cccaguucuc ggcccccg                                       88

<210> SEQ ID NO 65
<211> LENGTH: 88
<212> TYPE: RNA
<213> ORGANISM: Homo Sapiens

<400> SEQUENCE: 65
cgaggauggg agcugagggc ugggucuuug cgggcgagau gagggugucg gaucaacugg     60
ccuacaaagu cccaguucuc ggcccccg                                       88

<210> SEQ ID NO 66
<211> LENGTH: 84
<212> TYPE: RNA
<213> ORGANISM: Homo Sapiens

<400> SEQUENCE: 66
uugacuuagc ugguagugg ggaacccuuc caugaggagu agaacacucc uuaugcaaga      60
uucccuucua ccuggcuggg uugg                                           84

<210> SEQ ID NO 67
<211> LENGTH: 97
<212> TYPE: RNA
<213> ORGANISM: Homo Sapiens

<400> SEQUENCE: 67
cucaggugcu cuggcugcuu ggguuccugg caugcugauu ugugacuuaa gauuaaaauc     60
```

```
acauugccag ggauuaccac gcaaccacga ccuuggc                        97

<210> SEQ ID NO 68
<211> LENGTH: 86
<212> TYPE: RNA
<213> ORGANISM: Homo Sapiens

<400> SEQUENCE: 68
ugccagucuc uagguccug agacccuuua accugugagg acauccaggg ucacagguga  60
gguucuuggg agccuggcgu cuggcc                                     86

<210> SEQ ID NO 69
<211> LENGTH: 86
<212> TYPE: RNA
<213> ORGANISM: Homo Sapiens

<400> SEQUENCE: 69
ugccagucuc uagguccug agacccuuua accugugagg acauccaggg ucacagguga  60
gguucuuggg agccuggcgu cuggcc                                     86

<210> SEQ ID NO 70
<211> LENGTH: 72
<212> TYPE: RNA
<213> ORGANISM: Homo Sapiens

<400> SEQUENCE: 70
cuugggaaug gcaaggaaac cguuaccauu acugaguuua guaaugguaa ugguucucuu  60
gcuauaccca ga                                                    72

<210> SEQ ID NO 71
<211> LENGTH: 73
<212> TYPE: RNA
<213> ORGANISM: Homo Sapiens

<400> SEQUENCE: 71
cucugccucc cgugccuacu gagcugaaac acaguugguu uguguacacu ggcucaguuc  60
agcaggaaca ggg                                                   73
```